(12) United States Patent
Sandberg et al.

(10) Patent No.: US 8,352,289 B2
(45) Date of Patent: Jan. 8, 2013

(54) SYSTEMS AND METHODS FOR PROVIDING AND MAINTAINING ELECTRONIC MEDICAL RECORDS

(75) Inventors: Dale E. Sandberg, Springville, UT (US); Kyle B. Crandall, Springville, UT (US)

(73) Assignee: DHI Computing, Inc., Provo, UT (US)

( * ) Notice: Subject to any disclaimer, the term of this patent is extended or adjusted under 35 U.S.C. 154(b) by 220 days.

(21) Appl. No.: 12/853,289

(22) Filed: Aug. 9, 2010

(65) Prior Publication Data

US 2011/0054944 A1 Mar. 3, 2011

Related U.S. Application Data

(63) Continuation-in-part of application No. 09/476,415, filed on Dec. 30, 1999, now Pat. No. 7,774,210.

(51) Int. Cl.
*G06Q 50/00* (2006.01)
(52) U.S. Cl. .................................. 705/3; 705/2
(58) Field of Classification Search ................ 705/2, 3
See application file for complete search history.

(56) References Cited

U.S. PATENT DOCUMENTS

| | | | |
|---|---|---|---|
| 4,549,264 A | 10/1985 | Carroll et al. | |
| 4,553,206 A | 11/1985 | Smutek et al. | |
| 4,831,526 A | 5/1989 | Luchs et al. | |
| 4,893,270 A | 1/1990 | Beck et al. | |
| 5,072,383 A * | 12/1991 | Brimm et al. | 705/2 |
| 5,247,611 A | 9/1993 | Norden-Paul et al. | |
| 5,307,262 A * | 4/1994 | Ertel | 705/2 |
| 5,325,293 A | 6/1994 | Dorne | |
| 5,619,708 A | 4/1997 | Ho | |
| 5,664,207 A | 9/1997 | Crumpler et al. | |
| 5,682,526 A | 10/1997 | Smokoff et al. | |
| 5,704,371 A | 1/1998 | Shepard | |
| 5,732,221 A | 3/1998 | Feldon et al. | |
| 5,737,539 A | 4/1998 | Edelson et al. | |
| 5,745,712 A | 4/1998 | Turpin et al. | |
| 5,772,585 A | 6/1998 | Lavin et al. | |
| 5,781,442 A | 7/1998 | Engleson et al. | |
| 5,794,208 A | 8/1998 | Goltra | |
| 5,812,984 A | 9/1998 | Goltra | |
| 5,823,948 A | 10/1998 | Ross, Jr. et al. | |

(Continued)

OTHER PUBLICATIONS

Blackman, "The Usefulness of Handheld Computers in a Surgical Group Practice", Maters Thesis, Oregon Health Sciences University School of Medicine, May 1999.

(Continued)

*Primary Examiner* — Gerald J. O'Connor
*Assistant Examiner* — Neha Patel
(74) *Attorney, Agent, or Firm* — Kirton McConkie; David B. Tingey

(57) ABSTRACT

A customizable and dynamic electronic patient form and information system is provided having features whereby a healthcare provider may select and record various values corresponding to patient categories, the values being recorded as discrete data points at locations on a display that are reliable and predictive, and that are simultaneously displayed as selections on the patient form and as entries on a data logger or patient summary sheet. Further changes or modifications to the value are recorded as discrete data points and simultaneously displayed on the patient form and in the patient summary sheet. The patient form further includes features to permit a user to modify the form as desired to suit the needs of the patient and/or the healthcare provider's field of practice.

13 Claims, 29 Drawing Sheets

U.S. PATENT DOCUMENTS

| | | | |
|---|---|---|---|
| 5,823,949 | A | 10/1998 | Goltra |
| 5,832,450 | A | 11/1998 | Myers et al. |
| 5,835,897 | A | 11/1998 | Dang |
| 5,839,112 | A | 11/1998 | Schreitmueller et al. |
| 5,842,175 | A | 11/1998 | Andros et al. |
| 5,845,253 | A | 12/1998 | Rensimer et al. |
| 5,845,255 | A | 12/1998 | Mayaud |
| 5,899,998 | A | 5/1999 | McGauley et al. |
| 5,908,383 | A | 6/1999 | Brynjestad |
| 5,912,818 | A | 6/1999 | McGrady et al. |
| 5,924,074 | A | 7/1999 | Evans |
| 5,930,799 | A | 7/1999 | Tamano et al. |
| 5,946,659 | A | 8/1999 | Lancelot et al. |
| 5,950,168 | A | 9/1999 | Simborg et al. |
| 5,991,728 | A | 11/1999 | DeBusk et al. |
| 6,014,630 | A | 1/2000 | Jeacock et al. |
| 6,047,259 | A | 4/2000 | Campbell et al. |
| 6,055,541 | A | 4/2000 | Solecki et al. |
| 6,073,106 | A | 6/2000 | Rozen et al. |
| 6,081,786 | A | 6/2000 | Barry et al. |
| 6,151,581 | A | 11/2000 | Kraftson et al. |
| 6,272,468 | B1 * | 8/2001 | Melrose ............ 705/2 |
| 6,283,761 | B1 | 9/2001 | Joao |
| 6,338,039 | B1 | 1/2002 | Lonski et al. |
| 6,341,265 | B1 | 1/2002 | Provost et al. |
| 6,393,404 | B2 | 5/2002 | Water et al. |
| 6,401,072 | B1 | 6/2002 | Haudenschild et al. |
| 6,434,531 | B1 | 8/2002 | Lancelot et al. |
| 6,594,634 | B1 | 7/2003 | Hampton et al. |
| 7,774,210 | B1 | 8/2010 | Sandberg |

OTHER PUBLICATIONS

Dugas et al., "Intranet-Based Clinical Data Entry", Institute for Medical Informatics, University of Munich, D-81377 Munich Germany, 1999.

Melles et al., "User Interface Preferences in a Point-of-care Data System", Permanente Clinical Information Systems, Kaiser Permanente Northern California Region, 1998.

Ong et al., "Expert Clinical Interface", IEEE, Computers in Cardiology, 1995, pp. 765-768.

Trace et al., "Intelligent Medical Record—Entry (IMR-E)", Journal of Medical Systems, vol. 17, Nos. 314, 1993.

Hohnloser et al., "PADS (Patient Archiving and Documentation System): A Computerized Patient Record With Educational Aspects", International Journal of Clinical Monitoring and Computing 9, 1992, pp. 71-84.

* cited by examiner

Visit Form Entry

Eye Care Clinic    Visit # ___81___

| Appointment Date | Appointment Time | Account Number | Provider |
|---|---|---|---|
| 05-03-1999 | 09:00 | 1000 | Robert V. Coulter |

| Patient Name / SSN | | | Date of Birth / Age | | Home Phone | 888-111-444 |
|---|---|---|---|---|---|---|
| Anderson, Susan | F | 123456789 | 07-23-1977 | 21 | Work Phone | 888-111-444 |

| Address | 1234 Miller Rd | Insurance Company | Account Balance (prior to visit) |
|---|---|---|---|
| | Anywhere, KS 55555 | BCBS1 | 3,660.50 |

| EVALUATION AND MANAGEMENT SERVICES | | | MEDICAL DIAGNOSIS/TREATMENT | | RWC |
|---|---|---|---|---|---|
| New Patient | | | Foreign Body Removal (superficial) | 65205 | |
| Office Visit Level 1 - New Patient | 99210 | | Conjunctival Foreign Body Removal | 65210 | |
| Office Visit Level 2 - New Patient | 99202 | | Corneal Foreign BOdy Removal (w/o sit lamp) | 65220 | |
| Office Visit Level 3 - New Patient | 99203 | | Corneal Foreign BOdy Removal(w/sit lamp) | 65222 | |
| Office Visit Level 4 - New Patient | 99204 | | Scraping of cornea for culture | 65430 | |
| Office Visit Level 5 - New Patient | 99205 | | Removal of corneal epithelium(abrasion, cureliage) | 65435 | |
| Intermediate Exam - New Patient | 92002 | | With application of cheating agent | 65436 | |
| Comprehensive Exam - New Patient | 92004 | | Correction of Trichiasis, Epilation | 67820 | |
| Refraction - New Patient | 92015 | | Closure of Lacrimal Puncture by Plug | 68751 | |
| | | | Dilation of Lacrimal Puncture | 68800 | |
| Established Patient | | | Probing of Nasolacrimal Duct | 68820 | |
| Office Visit Level 1 - Established Patient | 99211 | | Probing of Lacrimal Canalicui | 68840 | |
| Office Visit Level 2 - Established Patient | 99212 | | Unlisted Procedure, lacrimal system | 68899 | |
| Office Visit Level 3 - Established Patient | 99213 | | Glucose screening | 62948 | |
| Office Visit Level 4 - Established Patient | 99214 | | Culture, Bacerial, Definitve, Blooding | 67040 | |
| Office Visit Level 5 - Established Patient | 99215 | | Culure or direct Bacerial Identification Method | 87072 | |
| Intermediate Exam - Est. Patient | 92012 | | Culutre, Bacterial,any source, Anaerobic | 87075 | |
| Comprehensve Exam - East. Patient | 92014 | | Culture, Fungi, Def. ID of each Fungus | 87101 | |
| RK Post OP | 99024 | | Smear, Primary Source | 87205 | |
| CAT Post Op | 56984 | | | | |
| | | | CONTACT LENS SERVICES | | |
| Special Ophthalmological Services | | | Fitting/Contact Lens, Material/Disease | 92070 | |
| Gonloscopy | 99210 | | CL Diagnosis/Adaption | 92310 | |
| Visual Field Limited | 92081 | | Aphakia (one eye) | 92311 | |
| Serial Tonometry | 92100 | | Aphakia (two eyes) | 92312 | |
| Ophthalmoscopy Ext. | 92225 | | Modification/Clean and Polish | 92325 | |
| Ophthalmoscopy, Sub. Ext. | 92226 | | OTHER - Contact Lens Materials | CL | |
| Fundus Photography | 92250 | | | | |
| Ophthalmodynamometry | 92260 | | GLASSES SERVICES | | |
| External Ocular Photography | 92285 | | Frame Services | FRAME | |
| | | | Ophthalmic Lens Treatment | LENS | |
| DIAGNOSIS | | | DIAGNOSIS | | |
| Astrignatism (regular) | 367.21 | | Allergic conjunctivie | 372.14 | |
| Astrignatism (irregular) | 367.22 | | Foreign Body - Conjunctivie | 930.10 | |
| Hyperopia | 367.0 | | Hemorrhage subconjunctival | 37272 | |
| Malingerer | V65.2 | | Cornea abrasion | 918.1 | |
| Myopia | 367.1 | | Black eye | 921.0 | |
| Presbyopia | 367.4 | | Blepharitis | 373.00 | |
| Spasm of accommodation | 367.53 | | Chalazion | 373.2 | |
| Suppression | 368.31 | | Allergic dermaltis | 373.32 | |
| Transient change | 367.81 | | Lid Lesion | 373.9 | |
| Aniseikonia | 397.32 | | Eye pain | 379.91 | |
| | | | Mascular degeneration | 362.50 | |
| Albinism | 270.2 | | Peripheral degeneration | 362.60 | |
| Amblyopia | 368.00 | | Retinal hole | 361.31 | |
| Arteriosclerosis | 440.9 | | Hemorrhage | 397.23 | |
| Asthenopia (photophobia) | 368.13 | | Vitreous Floaters | 379.24 | |
| Bells palsy | 351.0 | | | | |
| Burn of eye and adnexa | 940.9 | | Patient Co-Pay | COPAY | |
| Color deficiencies | 368.5 | | Personal Payment - Cash | PPCA | |
| Covergenca insufficiency | 378.8. | | Personal Payment - Check | PPCK | |
| Diabetes history | 250 | | Discount | DISC | |
| Diplopia | 368.2 | | | | |
| Dizziness | 780.4 | | | VISIT TOTAL | |

| 06/17/1999 | | | Eye Care Clinic | | | | Page 1 | |
|---|---|---|---|---|---|---|---|---|
| Transaction History For Accoint 1000 (Andersen, Jeremy) from 7 - 1999 ||||||||||
| Peroid | TranDate | Patient Name | Type | Code Description | Amount | Qty | Visit | Batch |
| 8-1999 | 06/17/1999 | Anderson, Susan | C | 99214 Office Visit Level 4-Eat Patient | 60.00 | 0 | 167 | VT |
| 8-1999 | 06/17/1999 | Anderson, Susan | A | BCWO BlueCross/Blue Shield Write-off | -10.00 | 0 | 167 | VT ADJ |
| 8-1999 | 06/17/1999 | Anderson, Susan | C | 65205 Foreign Body Removal | 60.00 | 0 | 167 | VT |
| 8-1999 | 06/17/1999 | Anderson, Susan | A | BCWO BlueCross/Blue Shield Write-off | -10.00 | 0 | 167 | VT ADJ |
| 8-1999 | 06/17/1999 | Anderson, Susan | C | 68899 Unlisted Procedure, lacrimal sys | 22.22 | 0 | 167 | VT |
| 8-1999 | 06/17/1999 | Anderson, Susan | C | V2020 COntact Lens Material | 20.00 | 0 | 167 | VT |
| 8-1999 | 06/17/1999 | Anderson, Susan | P | PPCK Personal Payment-Check | -50.00 | 0 | 167 | VT |
| 8-1999 | 06/17/1999 | Anderson, Susan | C | TAX Sales Tax | 1.25 | 0 | 167 | VT ADJ |
| 8-1999 | 06/17/1999 | Anderson, Susan | A | Disc Discount | -2.00 | 0 | 167 | VT |
| 8-1999 | | | | Subtotal for this Peroid | 91.25 ** | | | |
| | | | | Current Account Total Due | 3,751.75 *** | | | |

PCIS Medical Clinic

Guar: Jones, William  Visit # 274726

| Appt Date | Appt Time | Prov 17 | 01 | Acct No | Next Visit |
|---|---|---|---|---|---|
| 08-09-2010 | 09:11 AM | James Murdock | | 1 | ☐ Other |

| Patient Name / Birth Date / Age | | | Ref | Home Phone | 801123222 |
|---|---|---|---|---|---|
| Jones, Willie M | 09-09-2001 | 8 | PCP | Adtl Phone | |
| | M | 123-12-1234 | | | |
| 123 East Main | | 12345 | Insurance Company | Account Balance | 375.58 |
| Springville, UT 84663 | | | AET - Applied Med Ins | Co Pay Amount | 10.00 |
| | | | AAM - Medicare Accept | | |

| Code | Description | Fee | Code | Description | Fee |
|---|---|---|---|---|---|
| | OFFICE VISITS | | | | |
| | New Patient | | 90471 | Immunization Admin Single/Comb | |
| 99201 | Eval Manag New Pt Problem | | 90472 | Immunization Admin ea Additional Inj | |
| 99202 | Eval Manag New Pt Expanded | | 90632 | Hepatitis A Vaccination Adult | |
| 99203 | Eval Manag New Pt Detailed | | 90633 | Hepatitis A Vac Adoles 2 Dose | |
| 99204 | Eval Manag New Pt Comprehen | | 90669 | Pneumoncoccal Conjugate Vaccin | |
| 99205 | Eval Manag New Pt Complex | | 90723 | DTAP-HepB-IPV/Pediarix | |
| | Established Patient | | 90647 | HIB 3 dose Hemophilus influzena B ... | |
| 99211 | Eval Manag Estab Minimal Ser | | 90700 | DTAP Acell Pertus W DT | |
| 99212 | Eval Manag Est Prob Focused | | 90707 | MMR Measle/Mumps/Rubella Vac | |
| 99213 | Eval Manag Est Expanded Prob | | 90713 | Poliomyelitis Vaccine | |
| 99214 | Eval Manag Estab Detailed | | 90716 | Chicken Pox Varicella/Varivax | |
| 99215 | Eval Manag Established Pt Comprhc | | 90714 | DT Adult Decavac Preserv Free | |
| | WELL PERSON CARE | | 90715 | TdaP Adult Adacel 11-64 yrs | |
| | New Patient | | 90732 | Pneumovac Pneumococcal Immuniz | |
| 99381 | Prevent Med New Healthy <1 Yr | | 90734 | Menigococcal Vac Menactra A C Y ... | |
| 99382 | Prevent Med New Healthy 1-4 | | 90744 | Hapatitis B Vac Ped/Adolescent | |
| 99383 | Prevent Med New Healthy 5-11 | | 90746 | Hepatitis B Vaccine Adult | |
| 99384 | Prevent Med New Healthy 12-17 | | 90748 | Hepatitis B HIB Comvax | |
| 99385 | Prevent Med New Healthy 18-39 | | | | |
| 99386 | Prevent Med New Healthy 40-64 | | 90772 | Therapeutic Injection IM Subq | |
| 99387 | Prevent Med New Healthy >65 | | J1055 | Depo Provera Contracep 150 Mg | |
| | Established Patient | | J3301 | Kenalog per 10 Mg Triamcinalone | |
| 99391 | Well Child Periodic Eval <1 Yr | | J3420 | Vitamin B-12 To 1000 Mcg | |
| 99392 | Well Child Periodic Eval 1-4 | | J0696 | Rocephin 250 Mg Im | |
| 99393 | Well Child Periodic Eval 5-11 | | 86580 | TB Skin Test PPO Intradermal | |
| 99394 | Well Child Period Eval 12-17 | | | | |
| 99395 | Prevent Med Period Eval 18-39 | | 76805 | Ultrasound Preg Uterus Complete | |
| 99396 | Prevent Med Period Eval 40-64 | | 76815 | Ultrasound Preg Uterus Limited | |
| 99397 | Prevent Med Periodic Eval >65 | | | | |
| | PROCEDURES | | | | |
| 11100 | Biopsy Skin/Subq/Mm 1 Lesion | | OB | OB Visit | |
| 11101 | Biopsy Skin/Sub/Mm Ea Add Les | | | | |
| 11200 | Skin Tag Removal Up to 15 | | 99024 | Postop Visit | |
| 17000 | Destruct Les An Site 1St | | | | |
| 17003 | Destrust Less Meth 2014 Ea | | Code | Description | Flag |
| 17004 | Destruct Les Any Meth >15 Les | | | DIAGNOSIS | |
| 17110 | Destruct Warts Up To 14 Lesion | | 250.00 | Diabetes Noninsulin Depend Wo Co... | |
| 20550 | Tendon Sheath/Ligament Injection | | 275.41 | Hypocalcemia | |
| 20551 | Tendon Injection Origin/Insertion | | | | |
| 20552 | Trigger Point Injection 1/2 Muscle Gps | | | | |
| 20553 | Trigger Point Inj 3 or > Muscle Gps | | | DATE OF INJURY | |
| 20505 | Arthrocentesis Inermediate Joint | | | | |
| 20510 | Arthrocentesis Major Joint/Bursa | | | | |
| 45330 | Sigmoidoscopy Diagnostic | | Code | Description | Fee |
| 55250 | Vasectomy | | | PAYMENTS | |
| 69210 | Cerumen Revoal Impacted | | 001 | Check Co - Payment - Thank You | |
| 92552 | Audiometry Air Only | | 002 | Cash Co - Payment - Thank You | |
| 92567 | Tympanometry | | 01 | Check Payment - Thank You | |
| 94010 | Spirometry | | 02 | Cash Pyment -Thank You | |

PCIS Medical Clinic

| Guar: Jones, William | | | | | Visit # 274726 |
|---|---|---|---|---|---|
| Appt Date 08-09-2010 | Appt Time 09:11 AM | Prov 17 James Murdock | 01 | Acct No 1 | Next Visit ☐ Other |
| Patient Name / Birth Date / Age Jones, Willie M | | 09-09-2001  8 M  123-12-1234 | | Ref PCP | Home Phone 801123222 Adtl Phone |
| 123 East Main Springville, UT  84663 | | | 12345 | Insurance Company AET - Applied Med Ins AAM - Medicare Accept | Account Balance 375.58 Co Pay Amount 10.00 |

| Code | Description | Fee | Code | Description | Fee |
|---|---|---|---|---|---|
| | OFFICE VISITS | | 90471 | Immunization Admin Single/Comb | |
| | New Patient | | 90472 | Immunization Admin ea Additional Inj | |
| 99201 | Eval Manag New Pt Problem | | 90632 | Hepatitis A Vaccination Adult | |
| 99202 | Eval Manag New Pt Expanded | | 90633 | Hepatitis A Vac Adoles 2 Dose | |
| 99203 | Eval Manag New Pt Detailed | | 90669 | Pneumoncoccal Conjugate Vaccin | |
| 99204 | Eval Manag New Pt Comprehen | | 90723 | DTAP-HepB-IPV/Pediarix | |
| 99205 | Eval Manag New Pt Complex | | | | |

Visit Form Posting

Dept G   Batch No.

274726   Prov 17   Fac 01   [Discount] [Create Recall] [Cancel] [Post/Update]

Ins. AET   Willie Jones   [Hold Visit] [Add Text] [Skip This Visit] [Post W/Receipt]

| Tran CD | Description | Amount | Allowed | Pat. Resp | Ins. Due | Ins | Diags |
|---|---|---|---|---|---|---|---|
| 99201 ... | Eval & Manag New Pt Problem | 36.00 | 36.00 | 0.00 | 36.00 | Y | 250.00 |
| 99202 ... | Eval & Manag New Pt Expanded | 63.00 | 63.00 | 0.00 | 63.00 | Y | 250.00 |
| Total | | 99.00 | | 0.00 | 99.00 | | |

400

[Clear DX's] 250.00   Modifier Codes

| 99211 | Eval Manag E |
| 99212 | Eval Manag E |
| 99213 | Eval Manag E |
| 99214 | Eval Manag E |
| 99215 | Eval Manag E |
| 99381 | Prevent Med |
| 99382 | Prevent Med |
| 99383 | Prevent Med |
| 99384 | Prevent Med |
| 99385 | Prevent Med |
| 99386 | Prevent Med |
| 99387 | Prevent Med |
| 99391 | Well Child Per |
| 99392 | Well Child Per |
| 99393 | Well Child Per |
| 99394 | Well Child Per |
| 99395 | Prevent Med |
| 99396 | Prevent Med |
| 99397 | Prevent Med Periodic Eval >65 |

| Code | Description | | Code | Description | Flag |
|---|---|---|---|---|---|
| | PROCEDURES | | | | |
| 11100 | Biopsy Skin/Subq/Mm 1 Lesion | | OB | OB Visit | |
| 11101 | Biopsy Skin/Sub/Mm Ea Add Les | | | | |
| 11200 | Skin Tag Removal Up to 15 | | 99024 | Postop Visit | |
| 17000 | Destruct Les An Site 1St | | | | |
| 17003 | Destruct Less Meth 2014 Ea | | Code | Description | Flag |
| 17004 | Destruct Les Any Meth >15 Les | | | DIAGNOSIS | |
| 17110 | Destruct Warts Up To 14 Lesion | | 250.00 | Diabetes Noninsulin Depend Wo Co... | |
| 20550 | Tendon Sheath/Ligament Injection | | 275.41 | Hypocalcemia | |
| 20551 | Tendon Injection Origin/Insertion | | | | |
| 20552 | Trigger Point Injection 1/2 Muscle Gps | | | | |

FIG. 29

SYSTEMS AND METHODS FOR PROVIDING AND MAINTAINING ELECTRONIC MEDICAL RECORDS

RELATED APPLICATIONS

This application is a continuation-in-part of U.S. patent application Ser. No. 09/476,415, entitled "METHOD AND SYSTEM FOR RECORDING AND MAINTAINING PATIENT HISTORY DATA AS WELL AS GENERATING CONCURRENT BILLING RECORDS", which was filed in the United States Patent Office on Dec. 30, 1999, and which is incorporated herein by reference in its entirety.

BACKGROUND OF THE INVENTION

1. Field of the Invention

The present invention relates generally to maintaining medical records of patients within a health care organization and, more specifically, to maintaining and updating medical records in a computer networked system, including patient medical records and billing records. The present invention further relates to systems and methods that provide simultaneous tracking of activities relating to patient care by recording healthcare events as discrete data points that are simultaneously displayed in the patient record and shown as entries in a generated note or patient summary sheet.

2. Background and Related Art

Record keeping is critically important in the health care industry. The advent of the computer has been particularly helpful in the health care industry in keeping records that aid the health care provider in evaluating the patient's health and treatment history with that particular health care organization. Further, the recording of health care history for a group of patients is useful in conducting medical research for individuals having like symptoms and like treatments. Further still, there is an advantage of having computerized aids in managing costs and providing billing records for the health care provider, the patient, the insurance providers, as well as any governmental health care program such as, for example, Medicare.

However, while computerized health record technologies are currently available, challenges still exist. Accordingly, it would be an improvement in the art to augment or even replace current techniques with other techniques.

SUMMARY OF THE INVENTION

The present invention relates generally to maintaining medical records of patients within a health care organization and, more specifically, to maintaining and updating medical records in a computer networked system, including patient medical records and billing records. The present invention further relates to systems and methods that provide simultaneous tracking of activities relating to patient care by recording healthcare events as discrete data points that are simultaneously displayed in the patient record and shown as entries in a generated note or patient summary sheet.

A computer system is provided having features to accurately record, modify and update values corresponding to the examination of a patient by a healthcare provider. The computer system further includes features for simultaneously generating and updating a data logger or patient summary sheet to provide a summary of care given to the patient by the healthcare provider.

The healthcare provider first selects an electronic patient form from a database server or other storage device. The patient form is then rendered on an output device, such as a computer monitor or display. The healthcare provider then selects a sub-form corresponding to a system, a symptom, a disease or other parameter relating to the patient or care that can be given to the patient. The healthcare provider then examines the patient and selects or enters values into the sub-form as relating to the examination. Each value is recorded as a discrete data point and indicated on the sub-form as a number, a selection, a highlight, a figure, a drawing, a shape, etc. The discrete data point is simultaneously displayed as an entry on a patient summary sheet corresponding to the electronic patient form. Since the value is recorded as a discrete data point, any changes to the discrete data point are reflected in both the patient form and the patient summary sheet. In this way, the value as represented in the patient form is linked to the value as represented in the patient summary sheet.

In some implementations of the present invention, a value is simultaneously updated in the patient form and the patient summary sheet by selecting and updating the value in the patient file. A user may update the value either by directly selecting the value in the patient form, or by clicking on the value in the patient summary sheet which will directly link the user to the value in the patient form. By selecting the value in the patient summary sheet, the healthcare provider is quickly and accurately directed to the value in the patient form thereby saving time and preventing unnecessary sorting and searching through the patient form.

Finally, in some implementations of the present invention the patient form includes various features to permit on-the-fly user customization of the patient form and the various sub-forms, patient categories, selectable options, and the like. These features enable the healthcare provider to setup the patient form in a convenient format that is both useful in examining the patient, and practical based on the healthcare provider's field of practice. These features further enable the healthcare provider to create specialized entries, categories, forms, observations, conditions, and formats where such are not available for selection in the patient form. The healthcare provider is therefore able to establish and implement a patient form that is optimally suited for his or her professional needs.

Implementations of the present invention provide for a computerized medical record system that allows a healthcare provider to accurately and efficiently enter values corresponding to the examination and treatment of a patient, while simultaneously allowing for convenient and accurate creation of a patient summary sheet. The system provides a graphical user interface to guide the health care provider to understand steps that provide not only useful medical history records, but also clear and concise patient summary sheets that can be reviewed and relied upon as an accurate history of care given to patients, either to specific patients or to groups of patients having a similar characteristic. The system includes features to assist the healthcare provider in modifying and customizing the patient forms as required in order to meet the needs of the patient. The system also includes features to assist the healthcare provider in modifying and customizing the patient forms to meet the needs of the healthcare provider's field of practice.

These and other features and advantages of the present invention will be set forth or will become more fully apparent in the description that follows. The features and advantages may be realized and obtained by means of the instruments and combinations provided herein. Furthermore, the features and advantages of the invention may be learned by the practice of the invention or will be obvious from the description, as set forth hereinafter.

BRIEF DESCRIPTION OF THE DRAWINGS

In order to set forth the manner in which the above recited and other features and advantages of the present invention are obtained, a more particular description of the invention will be rendered by reference to specific embodiments thereof, which are illustrated in the appended drawings. Understanding that the drawings depict only typical embodiments of the present invention and are not, therefore, to be considered as limiting the scope of the invention, the present invention will be described and explained with additional specificity and detail through the use of the accompanying drawings in which:

FIGS. 14-17 illustrate various screenshots of an electronic patient form and corresponding patient summary sheet representing methods for customizing and updating the same in accordance with various representative embodiments of the present invention;

Figure 18:
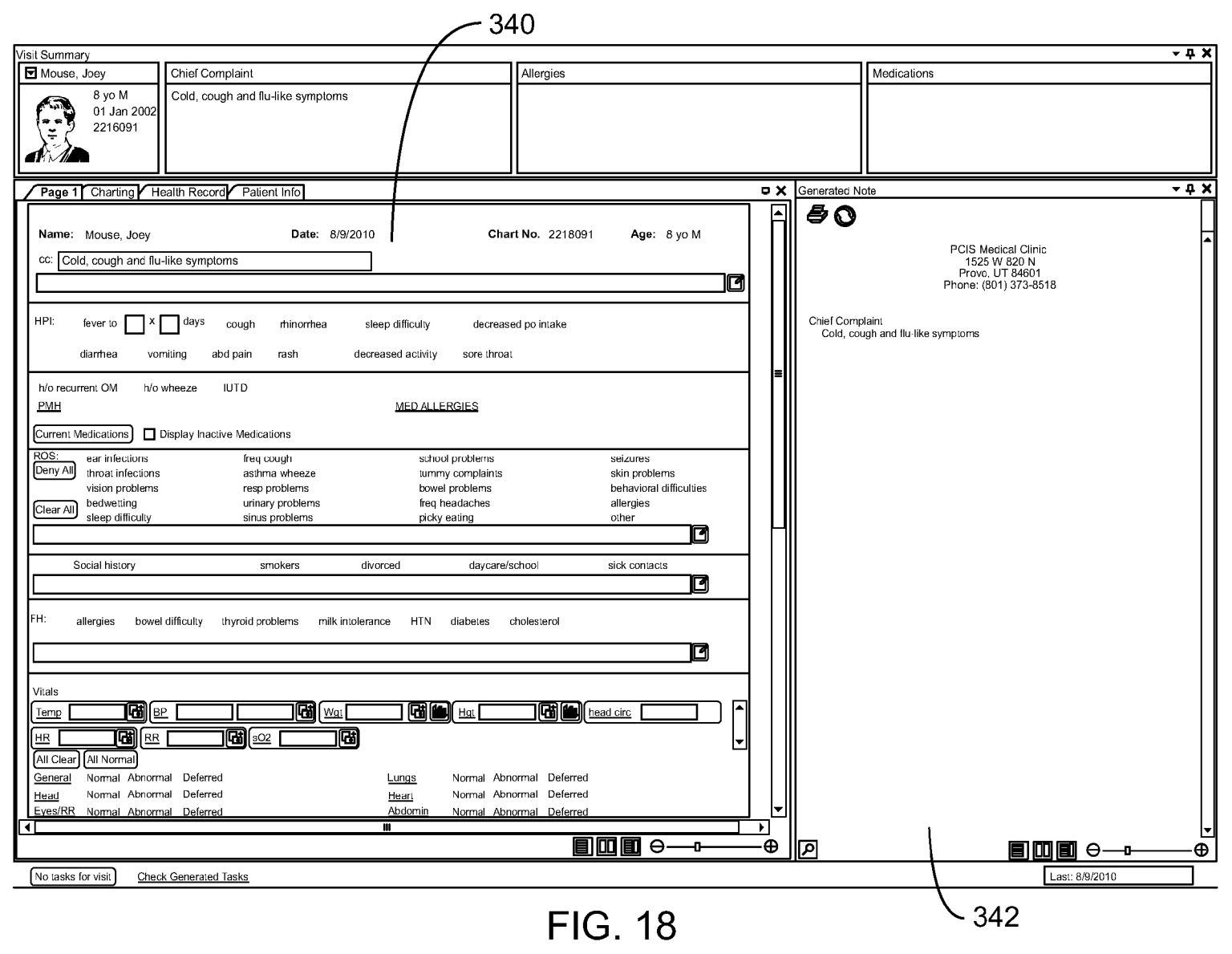
Figure 19:
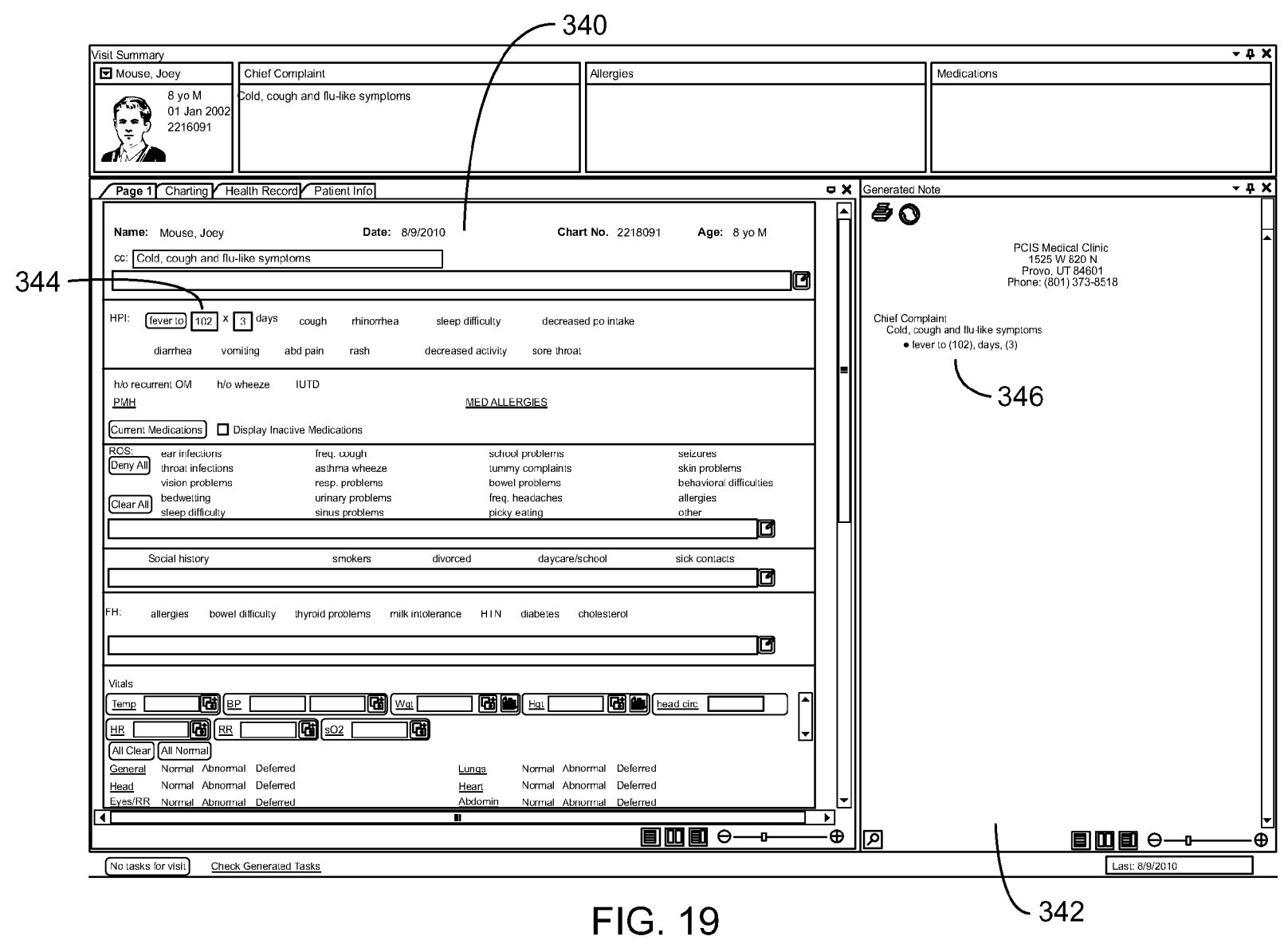
Figure 20:
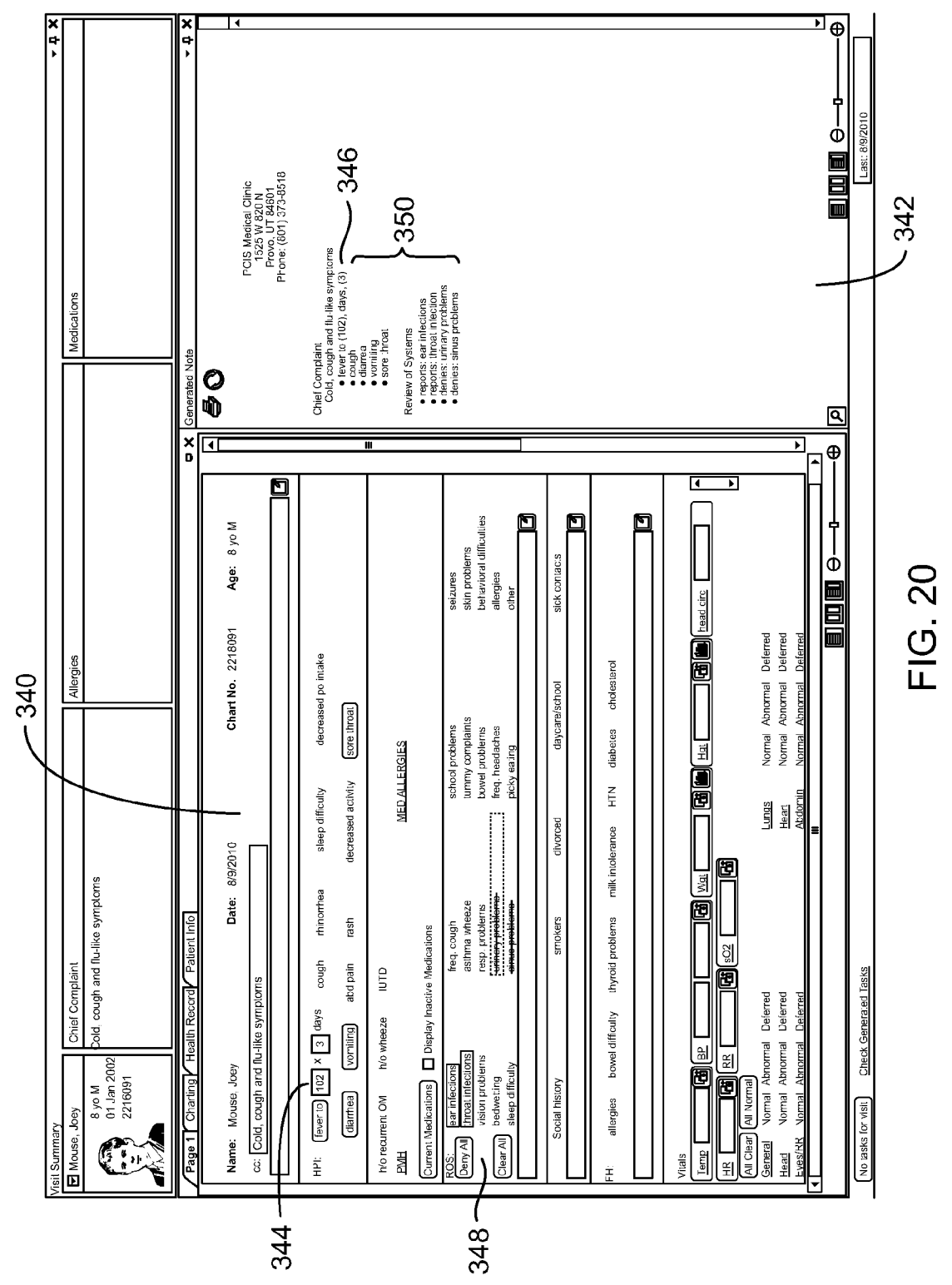
Figure 21:
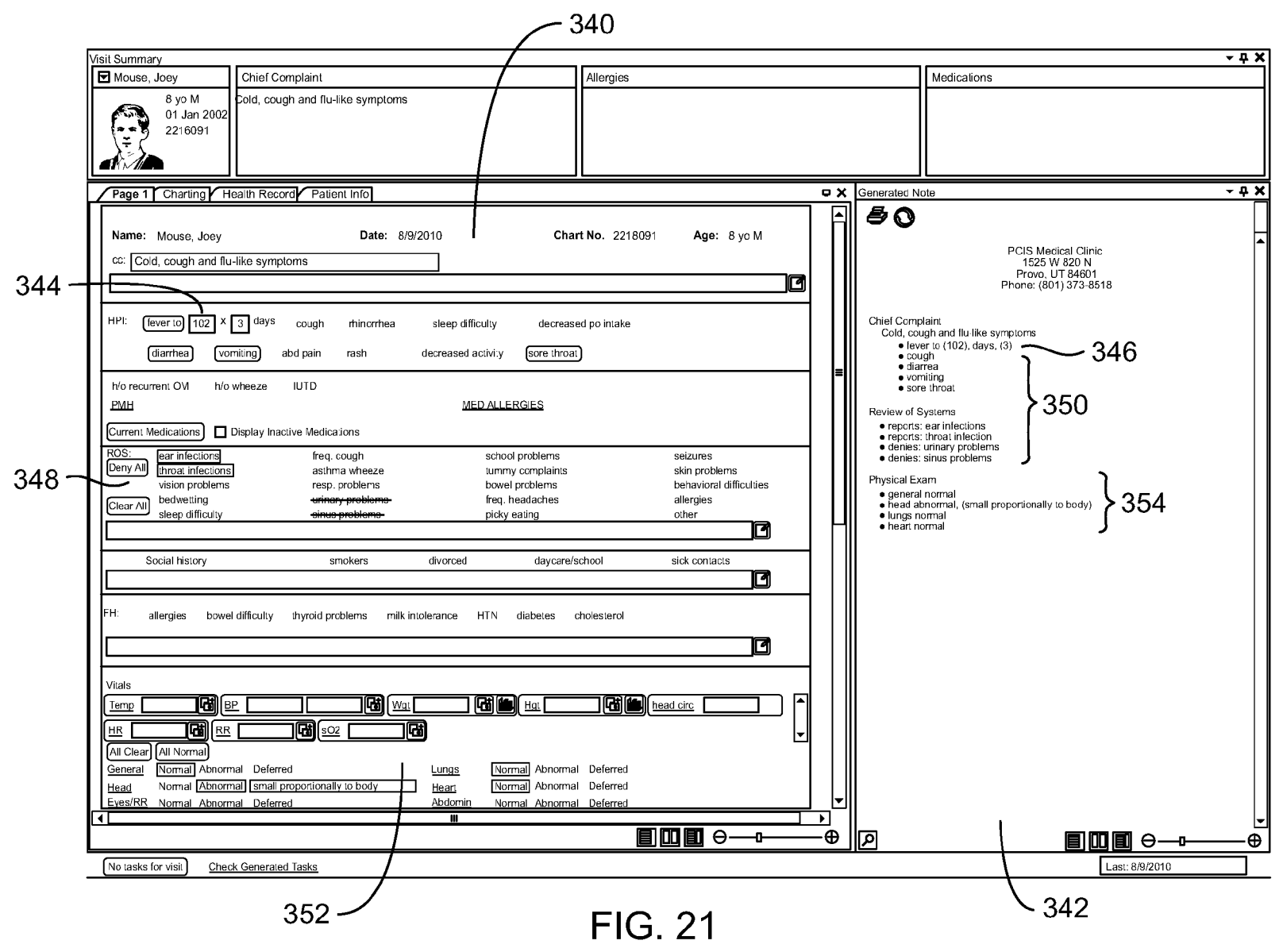

FIGS. 18-21 illustrate various screenshots of an electronic patient form and corresponding patient summary sheet representing methods for customizing and updating the same instantaneously or in real-time in accordance with a representative embodiment of the present invention, wherein the electronic patient form has discrete data points at locations on a display that are reliable, predictive, and familiar to the healthcare provider or other user;

FIGS. 22-23 illustrate screenshots of another electronic patient form and corresponding patient summary sheet representing methods for customizing and updating the same instantaneously or in real-time in accordance with a representative embodiment of the present invention, wherein the electronic patient form has discrete data points at locations on a display that are reliable, predictive, and familiar to the healthcare provider or other user;

FIG. 24 illustrates a screenshot of another electronic patient form and corresponding patient summary sheet representing methods for customizing and updating the same instantaneously or in real-time in accordance with a representative embodiment of the present invention, wherein the electronic patient form has discrete data points at locations on a display that are reliable, predictive, and familiar to the healthcare provider or other user;

FIG. 25 illustrates a representative patient or visit form utilized by a healthcare provider or other user such as during a patient conference and diagnosis in accordance with a representative embodiment of the present invention;

FIG. 26 illustrates the representative patient or visit form of FIG. 25 having a visit summary feature for use by a healthcare provider or other user during an office visit by a patient in accordance with a representative embodiment of the present invention;

FIG. 27 illustrates a representative record and billing summary printout for the patient after a visit with the health care provider or agent;

FIG. 28 illustrates another representative patient or visit form utilized by a healthcare provider or other user such as during a patient conference and diagnosis in accordance with a representative embodiment of the present invention; and FIG. 29 illustrates the representative patient or visit form of FIG. 28 having a visit form posting or visit summary feature for use by a healthcare provider or other user during an office visit by a patient in accordance with a representative embodiment of the present invention.

DETAILED DESCRIPTION OF THE PREFERRED EMBODIMENTS

Figure 1:
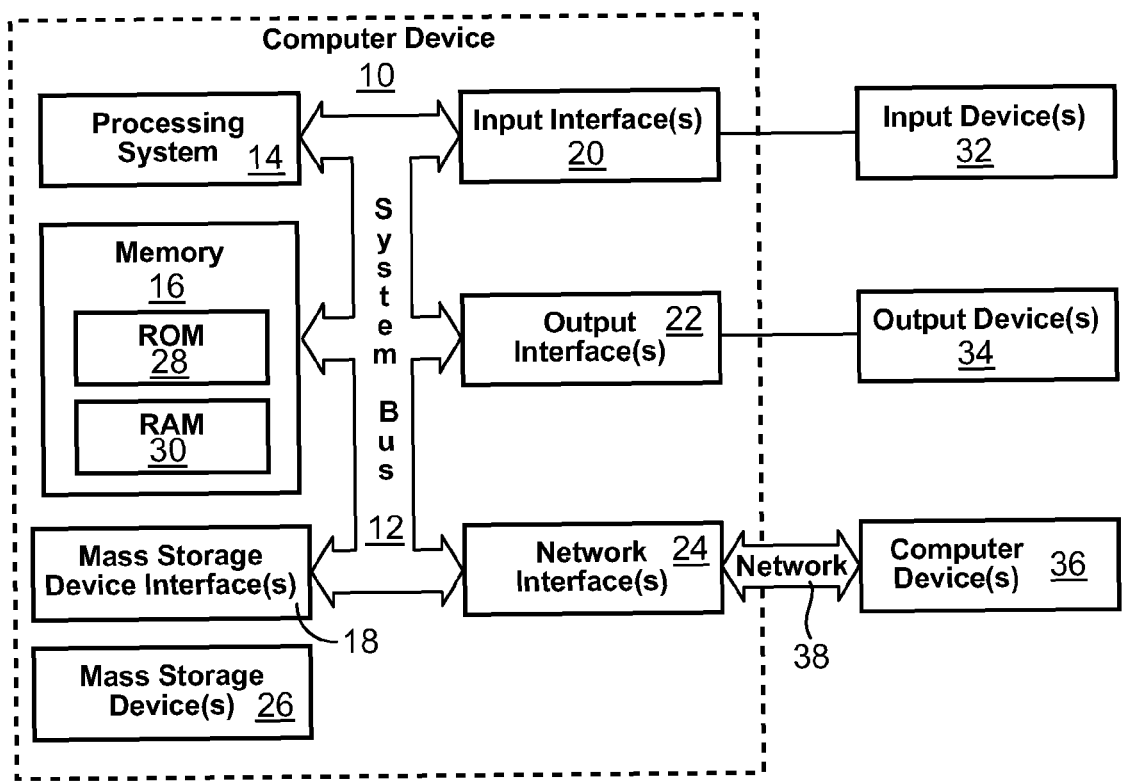
FIG. 1 illustrates a representative computer system upon which an embodiment of the present invention is implemented.

The present invention relates generally to maintaining medical records of patients within a health care organization and, more specifically, to maintaining and updating medical records in a computer networked system, including patient medical records and billing records. The present invention further relates to systems and methods that provide simultaneous tracking of activities relating to patient care by recording healthcare events as discrete data points that are simultaneously displayed in the patient record and shown as entries in a generated note or patient summary sheet.

Embodiments of the present invention relate to a computer system having features to accurately record, modify and update information corresponding to the examination of and the providing healthcare services to a patient by a healthcare provider. The computer system further includes features for simultaneously generating and updating a data logger or patient summary sheet to provide a summary of care given to the patient by the healthcare provider. The system provides a graphical user interface to guide the health care provider to understand steps that provide not only useful medical history records, but also clear and concise patient summary sheets that can be reviewed and relied upon as an accurate history of care given to patients, either to specific patients or to groups of patients having a similar characteristic.

Embodiments of the present invention further relate to the generation and utilization of dynamic and customizable patient forms having a reliable and predictive interface with data points that appear in a reliable and predictive location. Pick lists are utilized to efficiently provide information that is legible, accurate and complete. The storage of information as discrete data elements allows for reporting and statistical analysis, including in a data sanitized fashion as needed. The patient forms further include electronic scribble notes for text and/or hand drawn sketches.

Embodiments of the present invention include features to assist the healthcare provider in modifying and customizing the patient forms as required in order to meet the needs of the patient, and features to assist the healthcare provider in modifying and customizing the patient forms to meet the needs of the healthcare provider's field of practice. The customizable patient forms are dynamically created by an end user and provide common controls. Further the customizable patient forms, including patient charts, can be viewed by multiple people at the same time and at multiple locations.

Embodiments of the present invention include increased security in granting/denying access to information, enhanced tracking access of information and generation of security reports, increased backup and disaster recovery methods, and enhanced information sharing.

The following disclosure of the present invention is grouped into two subheadings, namely "Representative Operating Environment" and "Providing and Maintaining Electronic Medical Records." The utilization of the subheadings is for convenience of the reader only and is not to be construed as limiting in any sense.

Representative Operating Environment

FIG. 1 and the corresponding discussion are intended to provide a general description of a suitable operating environment in which embodiments of the present invention may be implemented. One skilled in the art will appreciate that embodiments of the present invention may be practiced by one or more computing devices and in a variety of system configurations, including networked configurations.

Embodiments of the present invention embrace one or more computer readable media, wherein each medium may be configured to include or includes thereon data or computer executable instructions for manipulating data. The computer executable instructions include data structures, objects, programs, routines, or other program modules that may be accessed by a processing system, such as one associated with a general-purpose computer capable of performing various different functions or one associated with a special-purpose computer capable of performing a limited number of functions. Computer executable instructions cause the processing system to perform a particular function or group of functions and are examples of program code means for implementing steps for methods disclosed herein. Furthermore, a particular sequence of the executable instructions provides an example of corresponding acts that may be used to implement such steps. Examples of computer readable media include random-access memory ("RAM"), read-only memory ("ROM"), programmable read-only memory ("PROM"), erasable programmable read-only memory ("EPROM"), electrically erasable programmable read-only memory ("EEPROM"), compact disk read-only memory ("CD-ROM"), or any other device or component that is capable of providing data or executable instructions that may be accessed by a processing system.

With reference to FIG. 1, a representative system for implementing the invention includes computer device 10, which may be a general-purpose or special-purpose computer. For example, computer device 10 may be a personal computer, a notebook computer, a tablet computer, a personal digital assistant ("PDA") or other hand-held device, a workstation, a minicomputer, a mainframe, a supercomputer, a multi-processor system, a network computer, a processor-based consumer electronic device, or the like.

Computer device 10 includes system bus 12, which may be configured to connect various components thereof and enables data to be exchanged between two or more components. System bus 12 may include one of a variety of bus structures including a memory bus or memory controller, a peripheral bus, or a local bus that uses any of a variety of bus architectures. Typical components connected by system bus 12 include processing system 14 and memory 16. Other components may include one or more mass storage device interfaces 18, input interfaces 20, output interfaces 22, and/or network interfaces 24, each of which will be discussed below.

Processing system 14 includes one or more processors, such as a central processor and optionally one or more other processors designed to perform a particular function or task. It is typically processing system 14 that executes the instructions provided on computer readable media, such as on memory 16, a magnetic hard disk, a removable magnetic disk, a magnetic cassette, an optical disk, or from a communication connection, which may also be viewed as a computer readable medium.

Memory 16 includes one or more computer readable media that may be configured to include or includes thereon data or instructions for manipulating data, and may be accessed by processing system 14 through system bus 12. Memory 16 may include, for example, ROM 28, used to permanently store information, and/or RAM 30, used to temporarily store information. ROM 28 may include a basic input/output system ("BIOS") having one or more routines that are used to establish communication, such as during start-up of computer device 10. RAM 30 may include one or more program modules, such as one or more operating systems, application programs, and/or program data.

One or more mass storage device interfaces 18 may be used to connect one or more mass storage devices 26 to system bus 12. The mass storage devices 26 may be incorporated into or may be peripheral to computer device 10 and allow computer device 10 to retain large amounts of data. Optionally, one or more of the mass storage devices 26 may be removable from computer device 10. Examples of mass storage devices include hard disk drives, magnetic disk drives, tape drives, flash drive and optical disk drives. A mass storage device 26 may read from and/or write to a magnetic hard disk, a removable magnetic disk, a magnetic cassette, an optical disk, or another computer readable medium. Mass storage devices 26 and their corresponding computer readable media provide nonvolatile storage of data and/or executable instructions that may include one or more program modules such as an operating system, one or more application programs, other program modules, or program data. Such executable instructions are examples of program code means for implementing steps for methods disclosed herein.

One or more input interfaces 20 may be employed to enable a user to enter data and/or instructions to computer device 10 through one or more corresponding input devices 32. Examples of such input devices include a keyboard and alternate input devices, such as a mouse, trackball, light pen, stylus, touch screen, or other pointing device, a microphone, a voice recognition device, a joystick, a game pad, a satellite dish, a scanner, a camcorder, a digital camera, and the like. Similarly, examples of input interfaces 20 that may be used to connect the input devices 32 to the system bus 12 include a serial port, a parallel port, a game port, a universal serial bus ("USB"), a firewire (IEEE 1394), or another interface.

One or more output interfaces 22 may be employed to connect one or more corresponding output devices 34 to system bus 12. Examples of output devices include a monitor or display screen, a speaker, a printer, and the like. A particular output device 34 may be integrated with or peripheral to computer device 10. Examples of output interfaces include a video adapter, an audio adapter, a parallel port, and the like.

One or more network interfaces 24 enable computer device 10 to exchange information with one or more other local or remote computer devices, illustrated as computer devices 36, via a network 38 that may include hardwired and/or wireless links. Examples of network interfaces include a network adapter for connection to a local area network ("LAN") or a modem, wireless link, or other adapter for connection to a wide area network ("WAN"), such as the Internet. The network interface 24 may be incorporated with or peripheral to computer device 10. In a networked system, accessible program modules or portions thereof may be stored in a remote memory storage device. Furthermore, in a networked system computer device 10 may participate in a distributed computing environment, where functions or tasks are performed by a plurality of networked computer devices.

Figure 2:
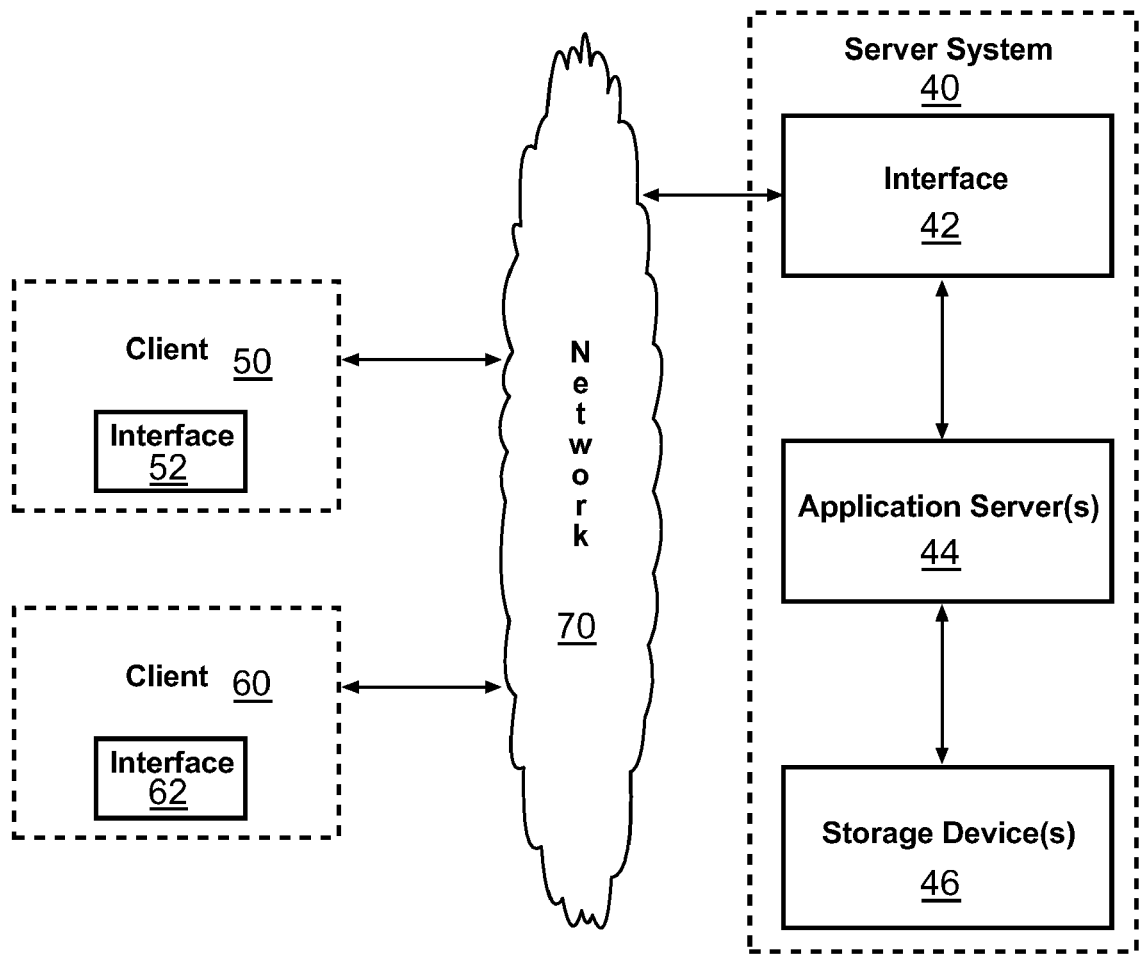
FIG. 2 is a representative networked computer system upon which an embodiment of the present invention is implemented.

While those skilled in the art will appreciate that the invention may be practiced in networked computing environments with many types of computer system configurations, FIG. 2 represents a representative embodiment of the present invention in a networked environment that includes clients 50 and 60 connected to one or more servers 40 via a network.

While FIG. 2 illustrates an embodiment that includes two clients 50 and 60 connected to the network 70, alternative embodiments include one client connected to a network or many clients connected to a network. Moreover, embodiments in accordance with the present invention also include a multitude of clients throughout the world connected to a network, wherein the network is a wide area network, such as the Internet.

FIG. 2 illustrates clients 50 and 60 that are able to access a server system 40 through network 70. Thus, in some embodiments a user employs client 50 to access a server system 40 to retrieve, edit and/or update healthcare service information as it relates to a condition, a diagnosis, a procedure, a treatment or a symptom of a patient. For example, in some embodiments a method of the present invention is employed in a web application that is remotely accessed through a web browser (i.e. interface 52) at a client device 50. Client 50 connects to network 70, which provides access to medical records containing the sought-after healthcare service information. Server system 40 is similar to client 50 in hardware configuration and provides access to a multitude of instructional medial to an end user at client 50. Further, server system 40 provides a digital medium for storing patient healthcare information as recorded by a healthcare provider. The healthcare provider as referred to herein may include any agent or individual provider, such as a doctor, a nurse, a medical assistant, a dentist, a dental assistant, a police officer and/or a paramedic. In some embodiments, server system 70 is configured to accommodate user input of healthcare information. The user as referred to herein may include any person from which healthcare information is obtained, recorded, accessed and/or stored by client 50 or 60.

Providing and Maintaining Electronic Medical Records

Embodiments of the present invention take place in association with healthcare services, specifically in association with generating, displaying and recording healthcare services information. In at least some embodiments, an electronic patient form, such as an electronic medical record, is accessed by a healthcare provider. An electronic patient form in accordance with the present invention may include any form, format or structure whereby information relating to a patient is stored electronically. In some embodiments, the electronic patient form comprises data entry points that appear in a reliable and predictive location and manner on the patient form. In some embodiments the electronic patient form comprises a digitized patient form having fillable fields to receive values corresponding to the condition, symptom, system, diagnosis, treatment or observation of the healthcare provider as relating to the patient. Still, in other embodiments the electronic patient form comprises an electronic document having a plurality of customizable fields wherein a healthcare provider modifies the fields to accurately represent the care being given to the patient. The electronic patient form may further include means for ordering a test or requesting further analysis for the patient by a separate healthcare provider, such as a specialist. The form may also include a notes section whereby a healthcare provider may provide detailed analysis or explanations which are not able to be accurately represented or recorded by other fields of the form. An electronic patient form in accordance with embodiments of the present invention may further include various dropdown menus, checklists, pictograms, pictographs, charts, diagrams, radiographs, scales, keyboards, fonts, bookmarks, symbols, links, URLs and other features to aid the healthcare provider in providing and recording healthcare procedures, treatments and diagnoses as may be required for any given area of health related services.

Once the patient form has been accessed, the healthcare provider modifies, updates and/or enters values relating to specific healthcare information of a patient. These values are then both simultaneously recorded as discrete data points and recorded in a data logger. Subsequent updates or additions to the patient form are likewise simultaneously recorded as discrete data points and recorded in the data logger. For example, if an existing value of the patient form is changed, the previous discrete data point is replaced with the new value, and the data logger is simultaneously updated to include the new value.

Embodiments of the present invention embrace systems and methods that provide for a complete electronic medical record system having features for simultaneous recordation of transpiring events in a data logger. This product covers the basic needs to access, evaluate and record values relating to healthcare information of a patient, while simultaneously tracking and recording these values in a data logger. This product further provides features whereby a specific healthcare parameter of a patient is easily accessed by selecting a discrete data point associated with the healthcare parameter as recorded in the data logger. Thus, a healthcare provider may access and update a healthcare parameter of a patient by either directly locating the parameter within the electronic patient form, or by selecting the discrete data point within the data logger and thereby being directed to the parameter within the electronic patient form.

In at least some embodiments, the electronic patient form comprises a plurality of forms, each form relating to a specific system of the patient. For example, in some embodiments the electronic patient form comprises a form relating to at least one of the cardiovascular system, the ocular system, the lymph system, the digestive system, the respiratory and circulatory systems, the musculoskeletal system, the nervous system, the immune system, the reproductive system, the auditory system, and the sensory system. In some embodiments, each form includes at least one fillable patient parameter or category relating to the system of the form.

For example, an ocular system form may include patient parameters relating to at least one of problems/complaints, general health, medications, medical allergies, eye history, family history such as diabetes, hypertension, cancer, glaucoma, cataracts, and armd, cover test results, color perception, general analysis, and visual acuity parameters including far and near OD, OS and OU for left and right eyes. An ocular system form may further include other parameters as commonly known and used by ocular healthcare providers.

One having skill in the art will appreciate that an electronic patient form in accordance with embodiments of the present invention may be adapted to include any form deemed necessary to examine, evaluate, diagnose, treat and track a system, condition or indication of a patient. The electronic patient form may further be adapted to include billing and insurance information, as well as general contact information for the patient. Thus, the examples given herein are merely representative embodiments and are in no way intended to limit the range of possible applications of the present invention.

A healthcare parameter of a patient's electronic patient form is generally updated following examination of the patient by a healthcare provider. For example, in some embodiments a healthcare provider initially accesses an electronic patient form of a patient from server system 40 (FIG. 2) via client 50 or 60. The healthcare provider may choose to review the patient form prior to examining the patient in order to refresh the healthcare provider's memory with regard to the various healthcare parameters of the patient. During the examination process of the patient, the healthcare provider selects a patient parameter from the patient form which relates to the type or kind of examination, procedure, diagnosis or treatment being performed on the patient. The healthcare provider then creates, enters, modifies or updates a value for the selected patient parameter. This value is then recorded as a discrete data point and simultaneously displayed in the patient parameter on the patient form, and shown in an associated data logger. Any subsequent changes to the value are likewise recorded as a discrete data point and simultaneously displayed in the patient parameter and shown in the associated data logger.

A data logger as used herein refers to an electronically generated note that displays summary details regarding changes made to the patient form as relating to activities performed by the healthcare provider. In some embodiments a data logger is generated by an executable program that links together the patient form and the data logger. Thus, any change or modification made to the patient form is instantaneously displayed as an event on the associated data logger. Likewise, in some embodiments the events of the data logger are editable whereby a healthcare provider may select and modify an event of the data logger thereby instantaneously updating the value for the associated patient parameter of the patient form. In some embodiments the patient form is accessed via a first executable program and the data logger is generated and maintained by a second executable program. In other embodiments, both the patient form and the data logger are generated and maintained by a first executable program.

In some embodiments the patient form and computer software for maintaining the same are stored on the server system 40 (FIG. 2) and accessed by clients 50 or 60 via network 70, while computer software for generating and maintaining the data logger are stored on clients 50 or 60 and updated via network 70. In other embodiments executable programs for both the data logger and the patient form are stored on server system 70 and access by clients 50 or 60 via network 70. Patient form and/or data logger are updated or modified via interfaces 52 or 62 of the respective clients 50 and 60.

Figure 3:
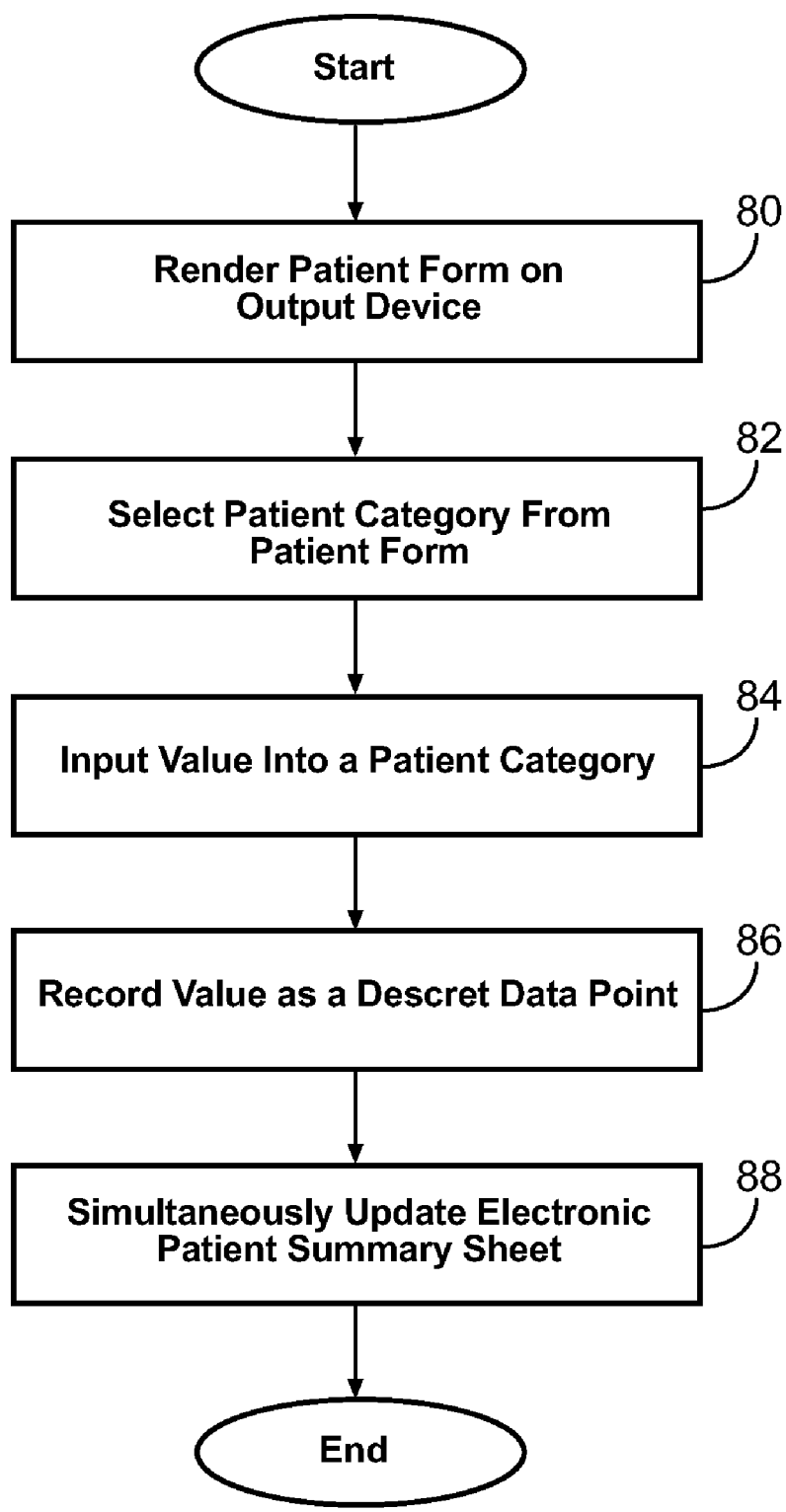
FIG. 3 is a flow diagram illustrating how an electronic patient form is prepared in accordance with a representative embodiment of the present invention.

Referring now to FIGS. 3-7, various flow charts are provided showing representative operations related to the input of patient parameter values in accordance with representative methods of the present invention. In FIG. 3, through computer device 10 (FIG. 1), a healthcare provider renders an electronic patient form on an output device 34 (step 80). The patient form may include a new or previously created patient form. In some embodiments the electronic patient form is rendered on a computer monitor following selection of the patient form from a database stored on the computer device 10 or server system 40.

The healthcare provider selects a patient category from the patient form that corresponds to the treatments, diagnosis, observation or examination of the patient (step 82). For example, if a patient is being examined for issues relating to the patient's circulatory system, the healthcare provider examines the patient and selects a patient category relating to the examination (i.e.: the patient's blood pressure). After determining a value for the patient category, the healthcare provider enters a value in the patient category relating to the patient parameters that was examined (step 84). The computer executable instructions record the value as a discrete data point associated with the selected patient category or parameter (step 86). The computer executable instructions further simultaneously record and associate the discrete data point as an entry on the patient summary sheet or data logger linked to the electronic patient form (step 88).

Figure 4:
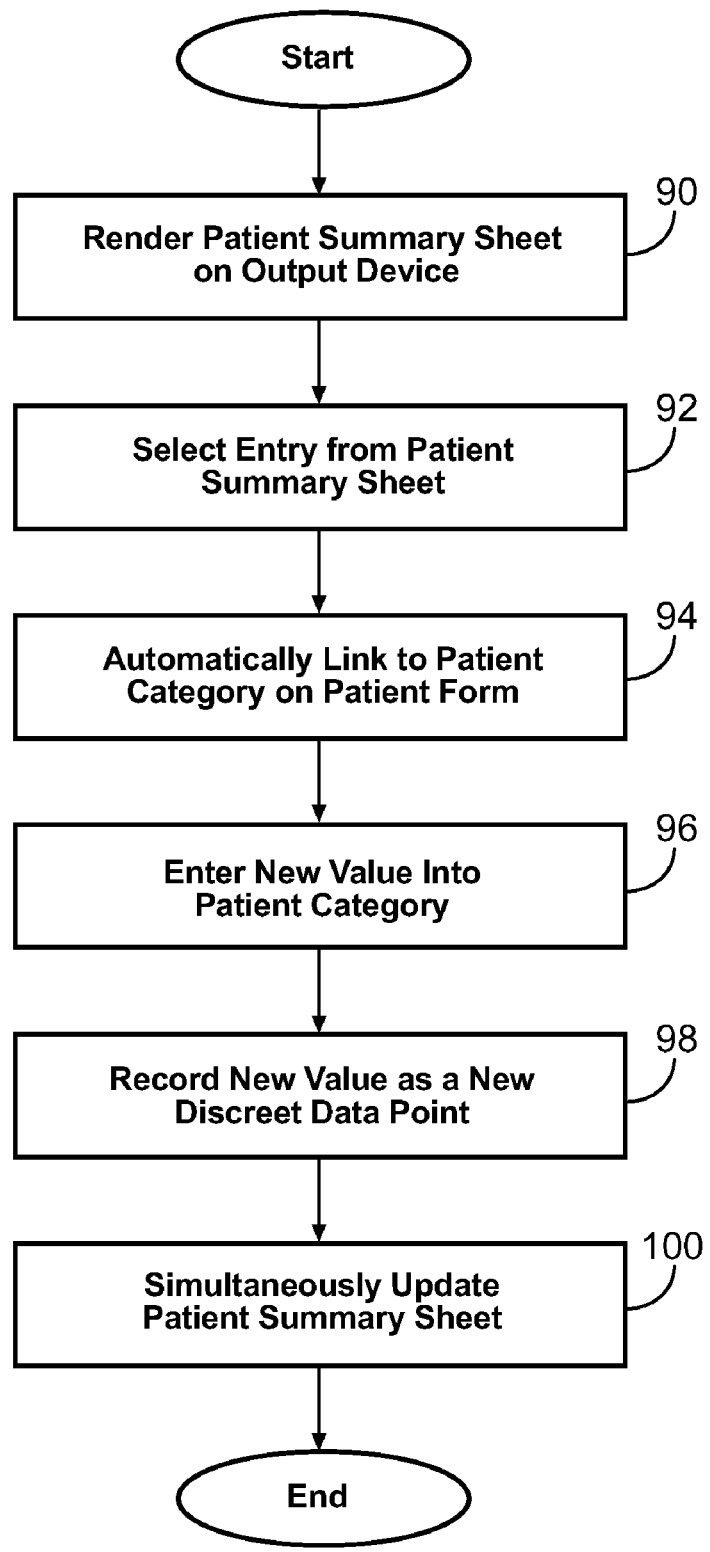
FIG. 4 is a flow diagram illustrating how an electronic patient form is prepared in accordance with a representative embodiment of the present invention.

In FIG. 4, a method for updating a pre-existing electronic patient form is shown. First, a healthcare provider renders a patient summary sheet or data logger linked to a pre-existing patient form on an output device 34 (step 90). The healthcare provider then selects an existing entry from the patient summary sheet (step 92). By selecting the existing entry, the pre-existing electronic patient form is rendered on the output device 34 such that the patient category represented by the existing entry is rendered on the output device 34 (step 94). The healthcare provider examines the patient and enters a new value in the patient category relating to the patient parameters that were most recently examined (step 96). The new value is recorded as a new discrete data point associated with the patient category (step 98). The new discrete data point is simultaneously associated with the patient summary sheet as a new entry indicating the activity of the healthcare provider relating to the patient category (step 100).

Figure 5:
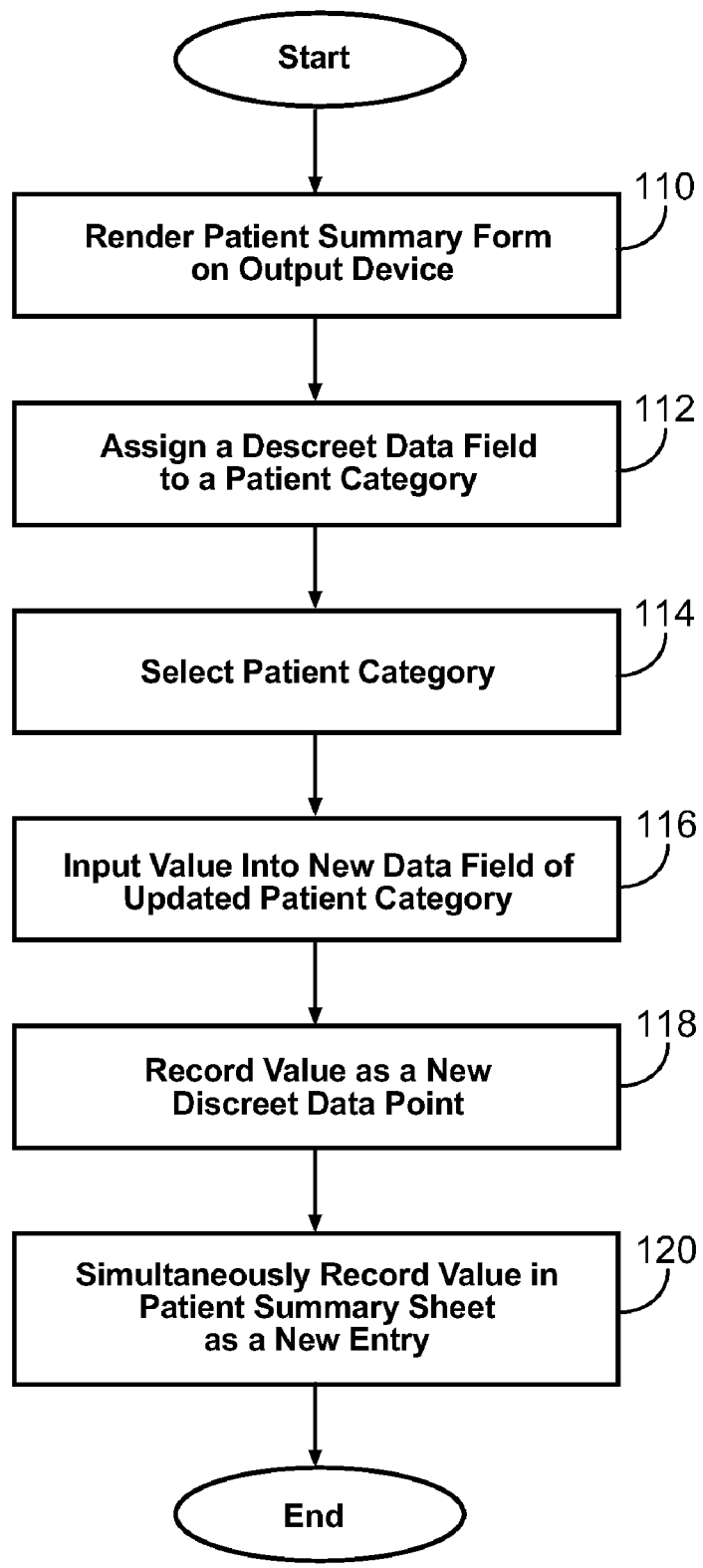
FIG. 5 is a flow diagram illustrating how an electronic patient form is updated in accordance with a representative embodiment of the present invention.

Referring now to FIG. 5, in some embodiments of the present invention a patient parameter or data field for a given patient category is not available on the electronic patient form. Therefore, the healthcare provider must edit the patient category to provide the needed field. Thus, an electronic patient form in accordance with some embodiments of the present invention includes features for dynamic setup or on-the-fly modification of the electronic form as required by the healthcare provider. In some embodiments the electronic patient form comprises features for augmenting checklists, dropdown menus, and selectable options to include new questions or options that may be edited by the healthcare provider. Thus, in the event that a healthcare provider is unable to accurately record the examination of the patient with the rendered patient form, the healthcare provider may modify the patient form to accurately reflect the care given to the patient. In some embodiments, the electronic patient form further comprises feature to permit the healthcare provider to remove data fields and/or patient categories that are irrelevant to the patient or the practice of the healthcare provider.

In FIG. 5, a healthcare provider first renders a patient form on an output device 34 (step 110). The healthcare provider selects a patient category and edits the category to include a desired data field (step 112). The healthcare provider saves the new data field and subsequently selects the updated patient category (step 114). The healthcare provider enters a value into the new data field of the updated patient category to accurately reflect the condition of the patient (step 116). The value is recorded as a discrete data point and associated with the updated patient category (step 118). The discrete data point is simultaneously associated with the patient summary sheet as a new entry indicating the activity of the healthcare provider relating to the patient category (step 120).

Figure 6:
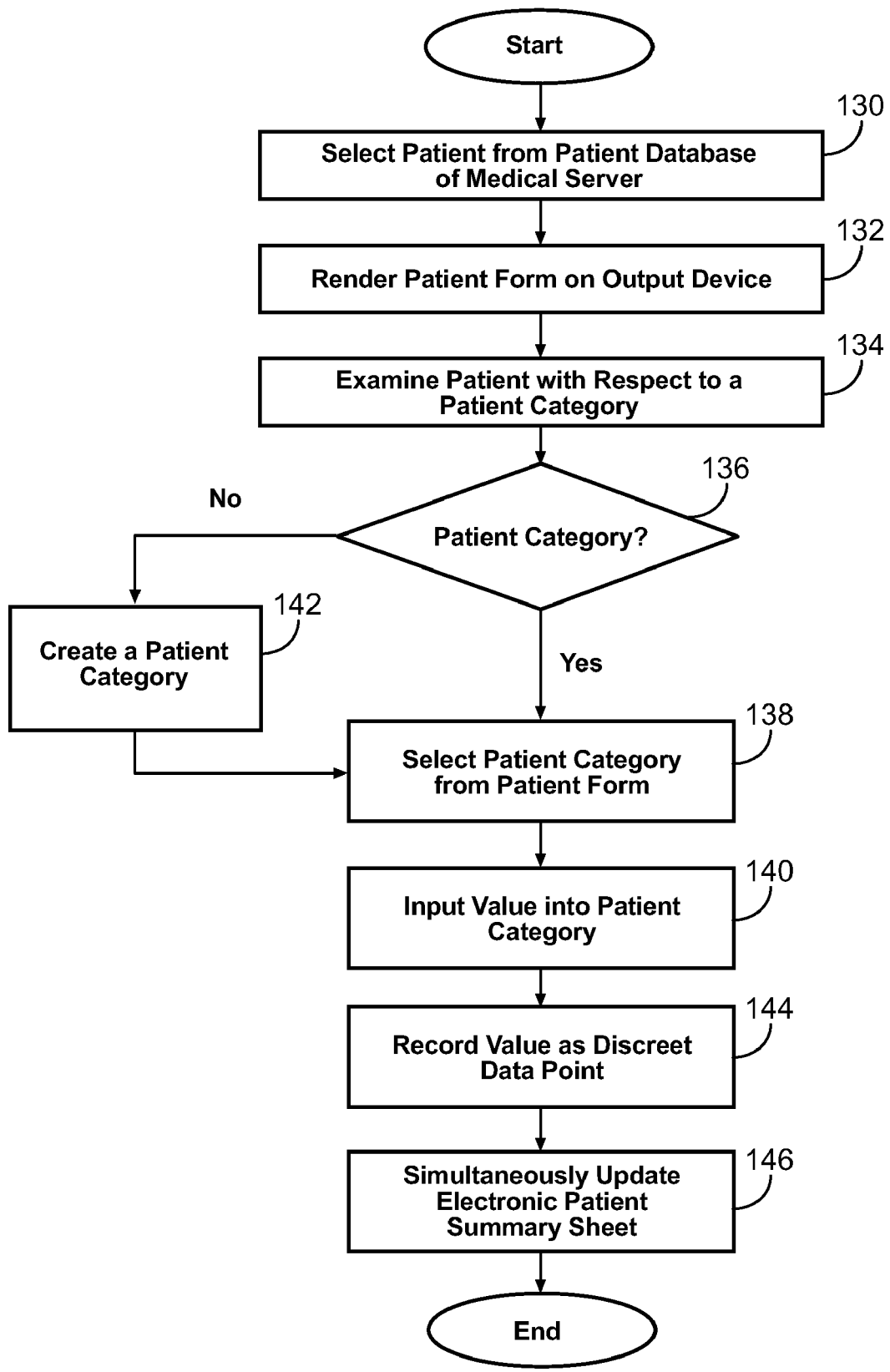
FIG. 6 is a flow diagram illustrating how an electronic patient form is prepared and updated in accordance with a representative embodiment of the present invention.

With reference to FIG. 6, at times it is desirable for the healthcare provider to add a new patient category to the electronic form to permit accurate reflection of the care provided and condition of the patient. Therefore, in some embodiments a healthcare provider first selects an electronic patient form of a patient from a patient database stored on a medical server system 40 (step 130). The patient form is then rendered on an output device 34, such as a client 50 or 60 accessed by the healthcare provider (step 132). The healthcare provider then examines the patient relative to a patient category (step 134). If a patient category is available, the healthcare provider selects the patient category from the patient form and enters a value as determined during the examination (decision block 136, step 138 and step 140). If a patient category is unavailable, the healthcare provider edits the electronic patient form to include the desired patient category (step 142). The healthcare provider then selects the new patient category and enters a value as determined during the examination of the patient (steps 138 and 140). The entered value is then recorded as a discrete data point that is simultaneously associated with the patient category and shown as an entry on the patient summary sheet or data logger (steps 144 and 146).

Figure 7:
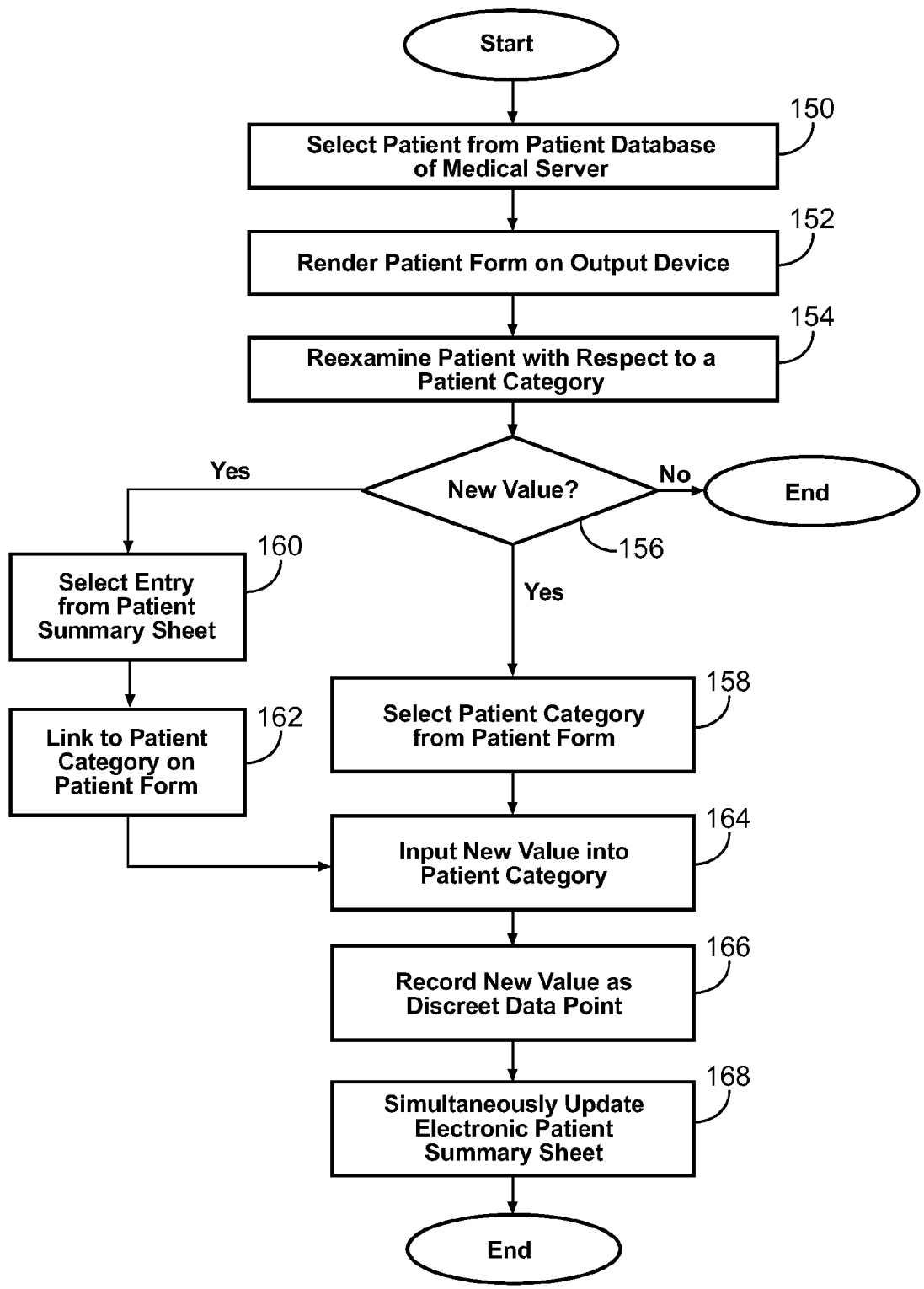
FIG. 7 is a flow diagram illustrating how an electronic patient form is prepared and modified in accordance with a representative embodiment of the present invention.

With reference to FIG. 7, in some embodiments a healthcare provider reexamines a patient to assess a patient parameter following a treatment or lapse of time. Therefore, in some embodiments a healthcare provider first selects an electronic patient form of a patient from a patient database stored on a medical server system 40 (step 150). The patient form is then rendered on an output device 34 (step 152). The healthcare provider then reexamines the patient with respect to the previously examined patient category (step 154). The healthcare provider then determines whether the condition of the patient requires that the patient category be updated to include a new value (decision block 156). If it is determined that a new value is not required, the healthcare provider may choose to provide an analysis or otherwise make a notation indicating that the condition of the patient remains the same. If the healthcare provider determines that the patient category requires an updated value, the healthcare provider may access the data field of the patient category by one of two methods. The first method is accomplished by locating the correct patient form and then directly selecting the patient category from the patient form (step 158). Alternatively, the healthcare provider may select the previous entry of the patient category, as displayed on the patient summary sheet, which will direct the healthcare provider to the patient category on the electronic patient form (steps 160 and 162). Once the patient category is access, the healthcare provider then enters the new value into the patient category (step 164). The new value is then recorded as a discrete data point that is simultaneously associated with the patient category and shown as an entry on the electronic patient summary sheet or data logger (steps 166 and 168).

The features of embodiments of the present invention provide means of accurately recording and simultaneously tracking the activities of the healthcare provider as relating to a patient. In some embodiments of the present invention, the patient summary sheet is saved following examination of the patient and is thereafter preserved as a record or generated note detailing the care given to the patient. In some embodiments it is desirable to prevent post modification of previous data entries as recorded in the patient summary sheet. When a healthcare provider updates a previous value of a patient category, the new value is recorded as a new event on the patient summary sheet. Thus, the new value and the previous value are shown as separate entries or events on the patient summary sheet, each entry having a separate value.

Referring now to FIGS. 8-17 various screenshots are provided to demonstrate a representative method of implementing an embodiment of the present invention. One having skill in the art will appreciate that the features of the present invention may be implemented in any variety of possible formats and steps to achieve a similar outcome, and therefore the foregoing example is not intended to limit the scope of the present invention.

Figure 8:
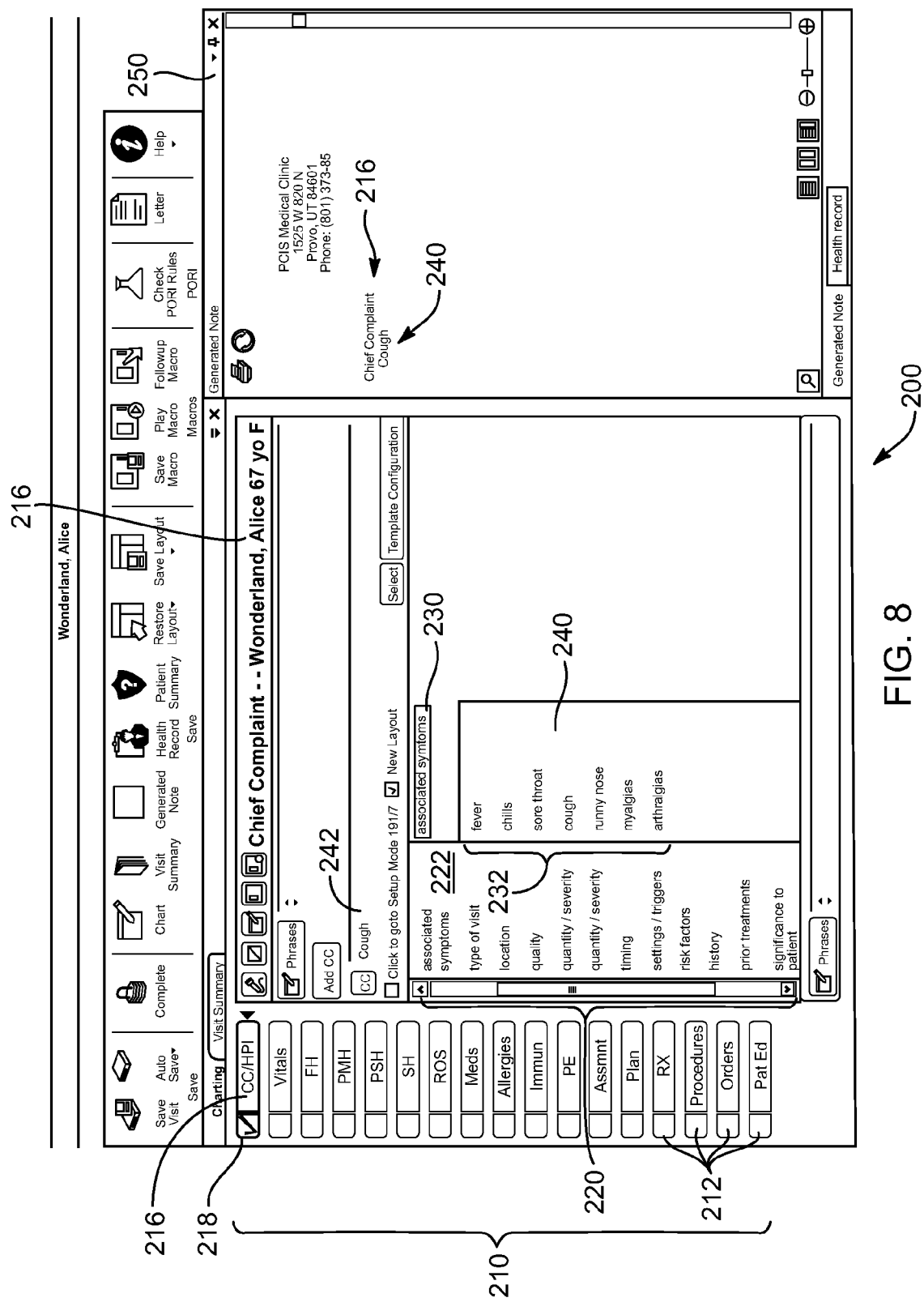
FIGS. 8-13 illustrate various screenshots of a representative electronic patient form and corresponding patient summary sheet representing methods for preparing, modifying and updating the same in accordance with various representative embodiments of the present invention.

Referring now to FIG. 8, a representative embodiment of an electronic patient form 200 is shown as rendered on a display or monitor. Patient form 200 comprises a plurality of sub-forms 210 shown as selectable tabs 212. Each tab 212 includes a set of initial to indicate the type of information or system represented on the sub-form 210. For example, in some embodiments a sub-form 216 is provided to record and track the patient's chief complaint and history of present illness (CC/HPI). A checkbox 218 is provided adjacent to each tab 212 so as to indicate the sub-form 210 selected by the healthcare provider.

Upon selecting a sub-form 216, a checkmark or other indicator appears in the checkbox 218, and the respective sub-form 216 is displayed on the patient form 200. A set of selectable patient categories 220 is displayed. The set of categories 220 correspond to the activity of the selected sub-form 216. Upon selecting a patient category 222, a pick list or dropdown menu 230 is provided having a plurality of selectable options 232, each option corresponding to the patient category 222. Upon selecting a corresponding option 240, the option 240 is recorded as a discrete data point and displayed on the sub-form 216 in an appropriate field 242. Additionally, the discrete data point is linked to the data logger or patient summary sheet 250 to create a generated note. The entry for the patient summary sheet 250 includes information regarding the selected sub-form 216 and the value or selected option 240 under the sub-form.

Figure 9:
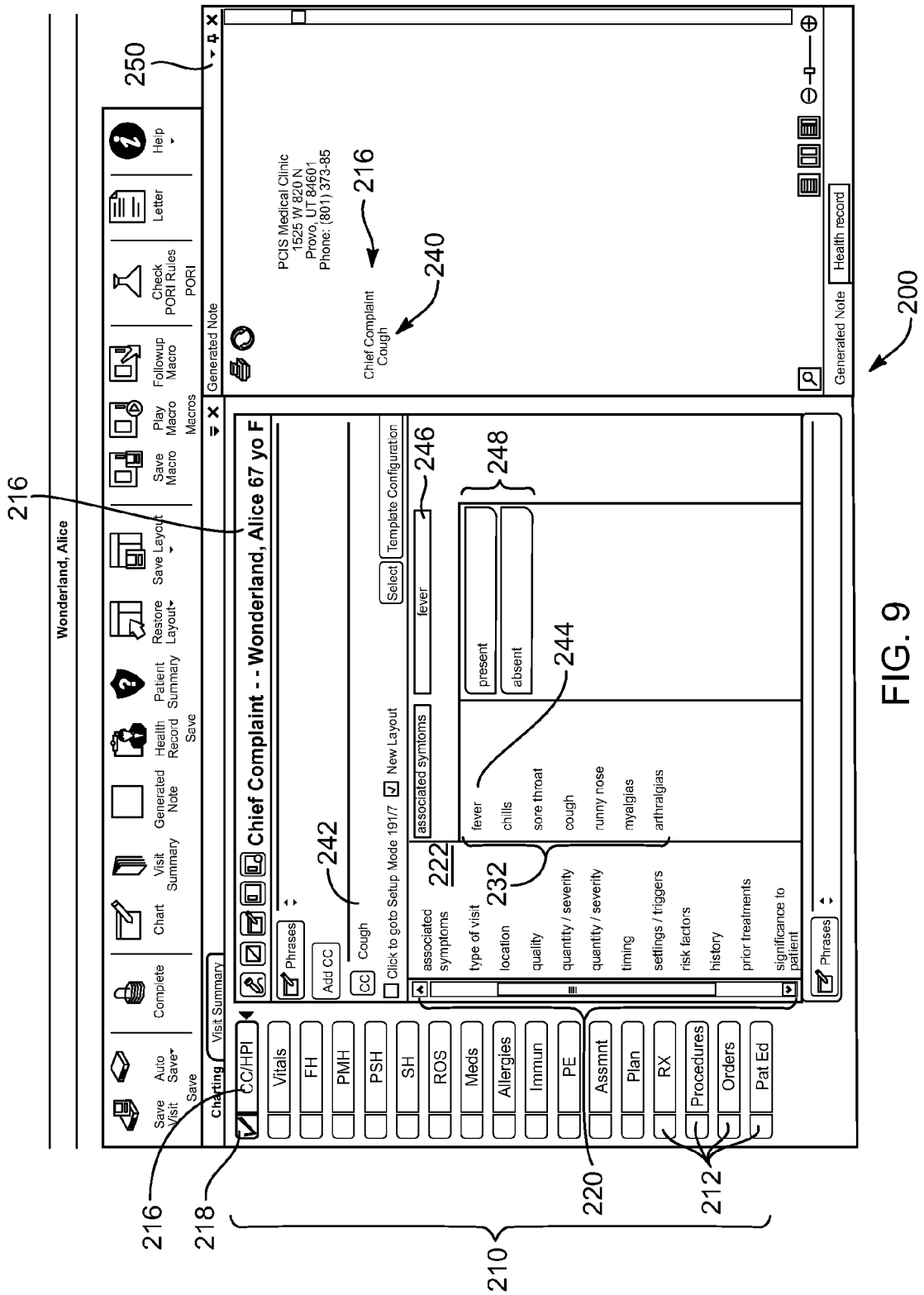
Figure 10:
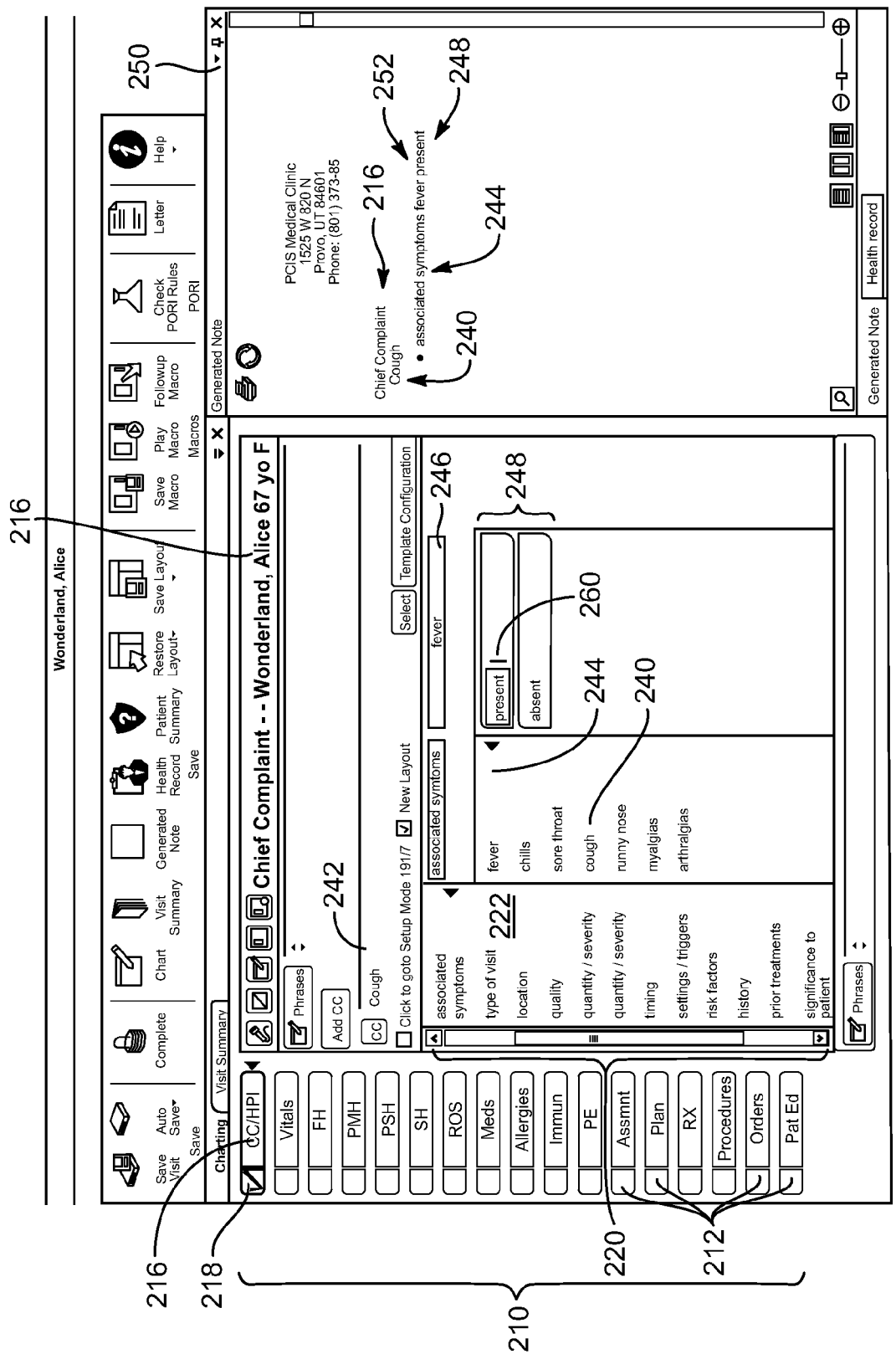

In some embodiments selection of an option 244 provides a dropdown menu 246 having a plurality of additional selectable options 248, as shown in FIG. 9. Upon selection of an option 248, the value is recorded as a discrete data point and displayed within the dropdown menu 246 as a circled selection, as shown in FIG. 10. The value is further and simultaneously displayed as an entry 252 in the patient summary sheet 250. In some embodiments the selectable option 248 further includes a field 260 whereby a healthcare provider may enter a value or additional information regarding the option 248. For example, in some embodiments the healthcare provider enters a numerical value in field 260 to represent the temperature of the patient. Upon entering a value into field 260, the value is recorded as a discrete data point and simultaneously displayed on the patient summary sheet 250.

Figure 11:
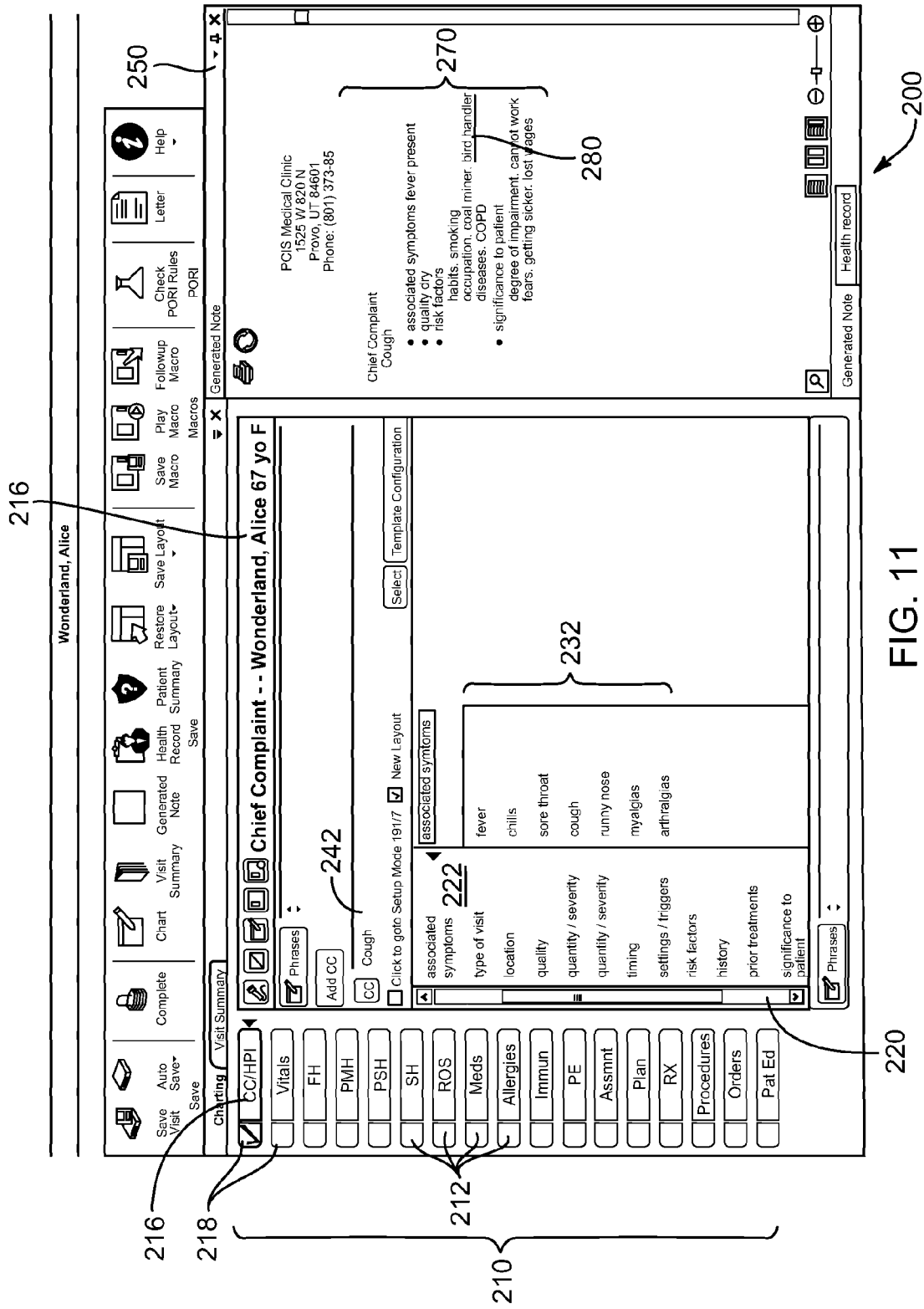

As the examination of the patient progresses, the healthcare provider continues to update the patient form 200 by selecting the necessary sub-forms 210, patient categories 220, selectable options 232, sub-selectable options 248 and so forth as required. Each selection or action of the healthcare provider is recorded as a discrete data point and simultaneously linked to and represented on the patient summary sheet 250. This results in the formation of a generated note including a summary 270 detailing the care given to the patient, as shown in FIG. 11.

Figure 12:
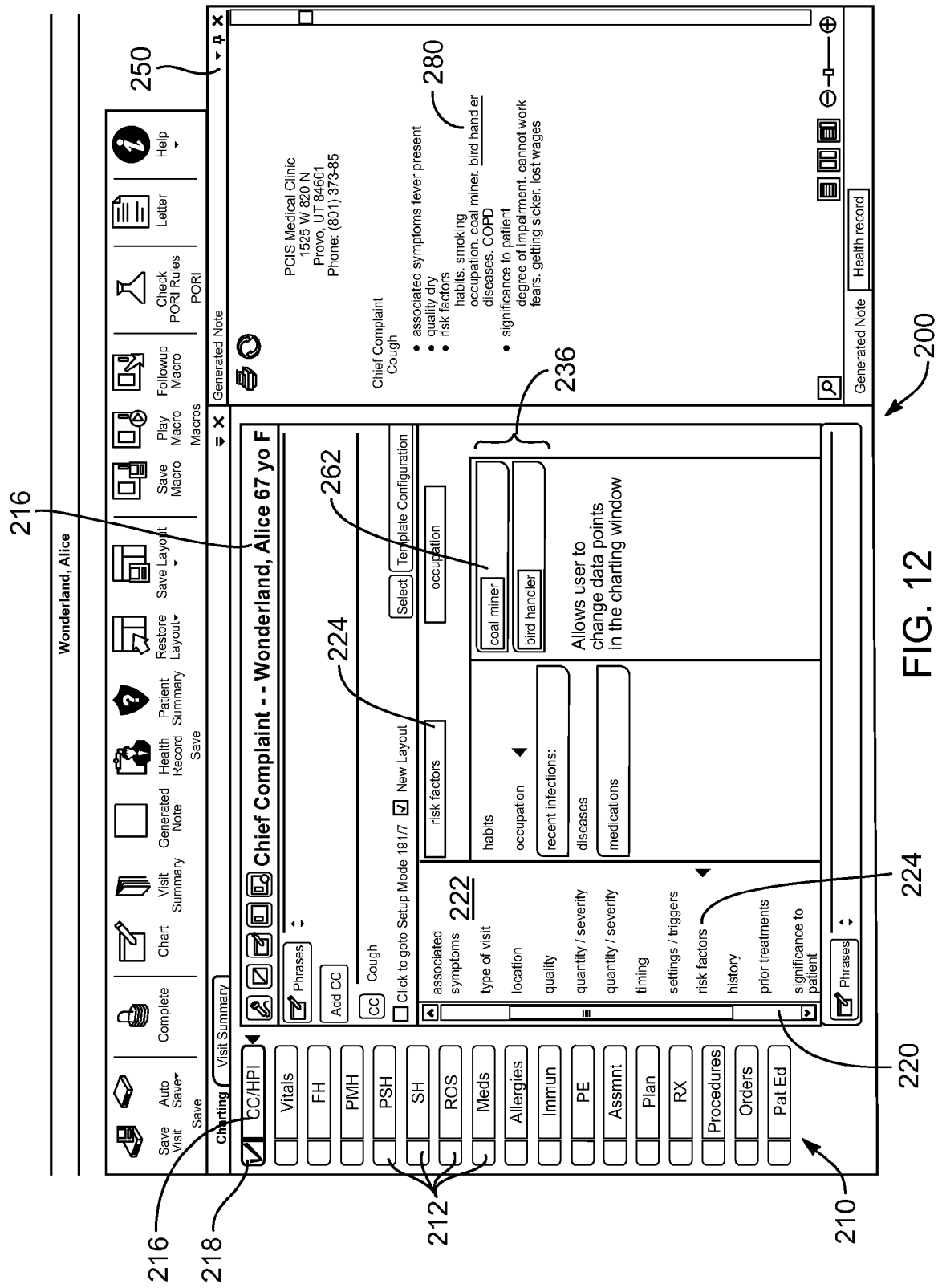
Figure 13:
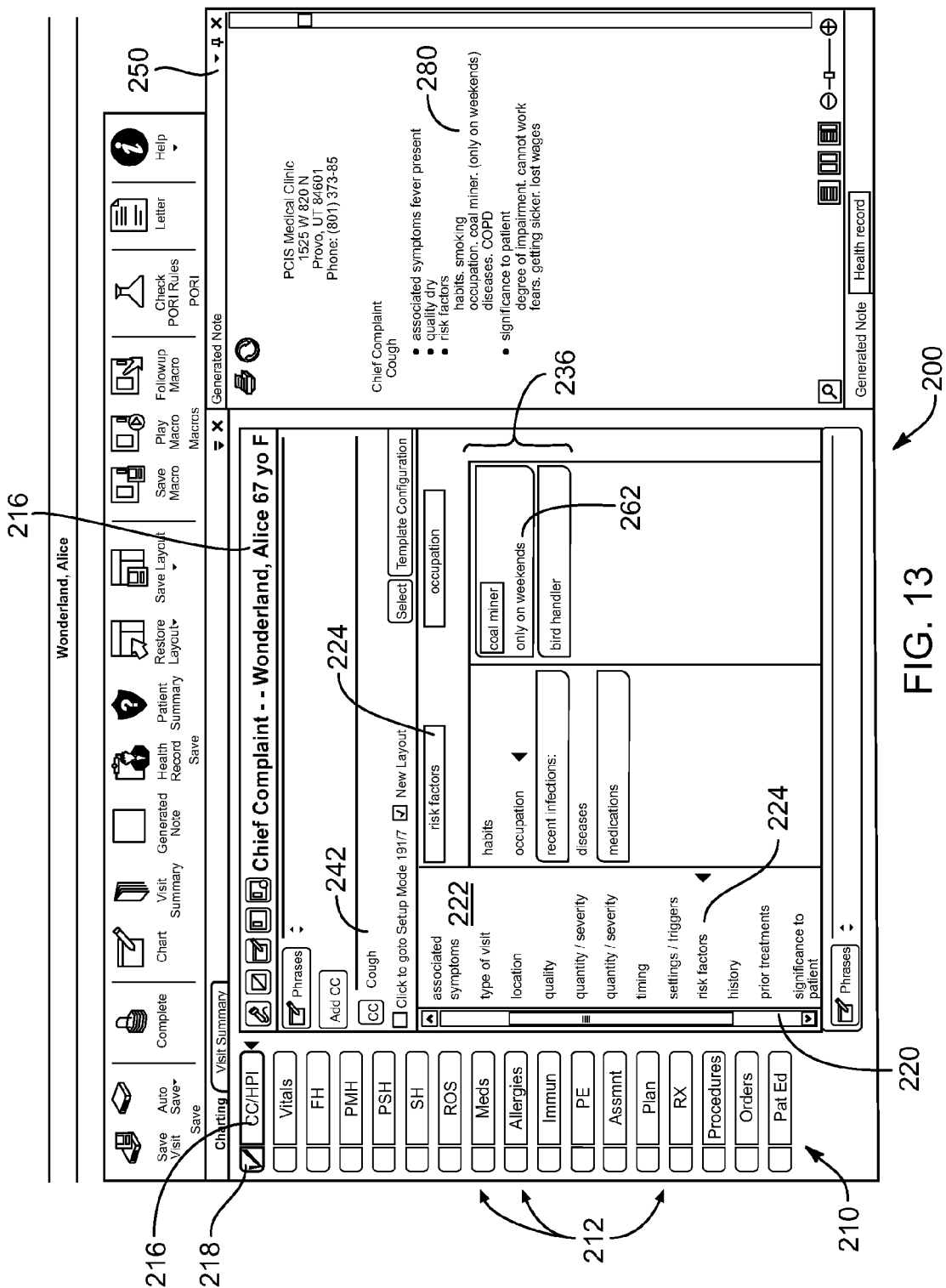

Prior to the end of the patient examination, a healthcare provider may modify any entry represented in the patient summary sheet 250 by first selecting a desired entry 280. In this example, the healthcare provider desires to enter additional details relative the occupation of the patient as a bird handler. Upon selecting the desired entry 280, the patient sub-form 216 is updated or rendered to display the appropriate patient category 224, and previously selected options 236, as shown in FIG. 12. The healthcare provider is then permitted to update the selection by entering additional information or values into field 262, as shown in FIG. 13. The respective entry on the patient summary sheet 250 is simultaneously updated to include the additional information of field 262. The additional information is also recorded and stored as a discrete data point, in accordance with above teaching.

Figure 15:
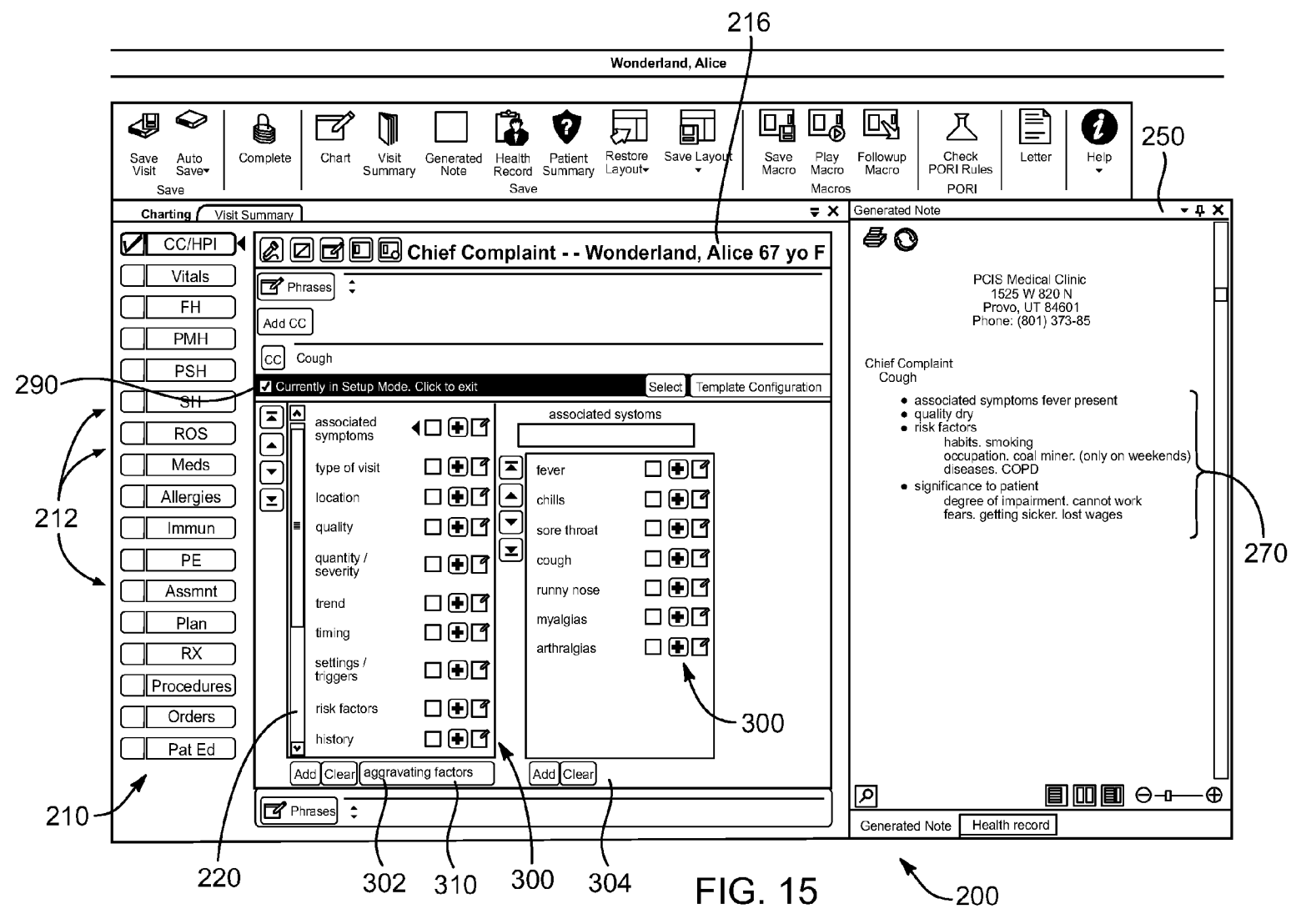
Figure 16:
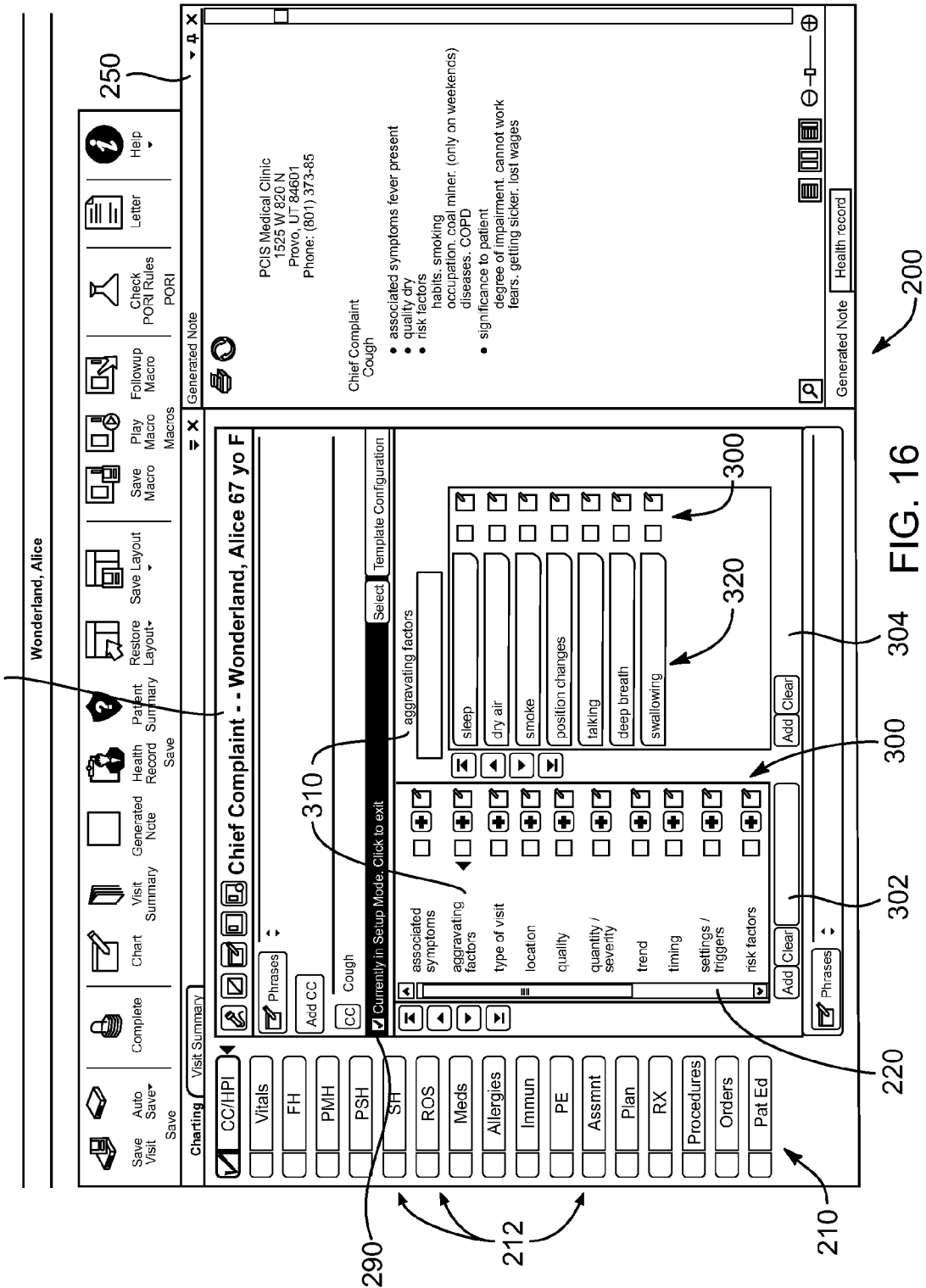

In some embodiments of the present invention, the electronic patient form 200 may be modified by a user to include desired patient categories, sub-categories, options, sub-options, and so forth as may be required to customize the form 200 to a patient's needs and/or a healthcare provider's field of practice. Thus, a patient form 200 in accordance with some embodiments of the present invention include an option for setting up the form to a desired format, as shown in FIGS. 14 through 16.

Figure 14:
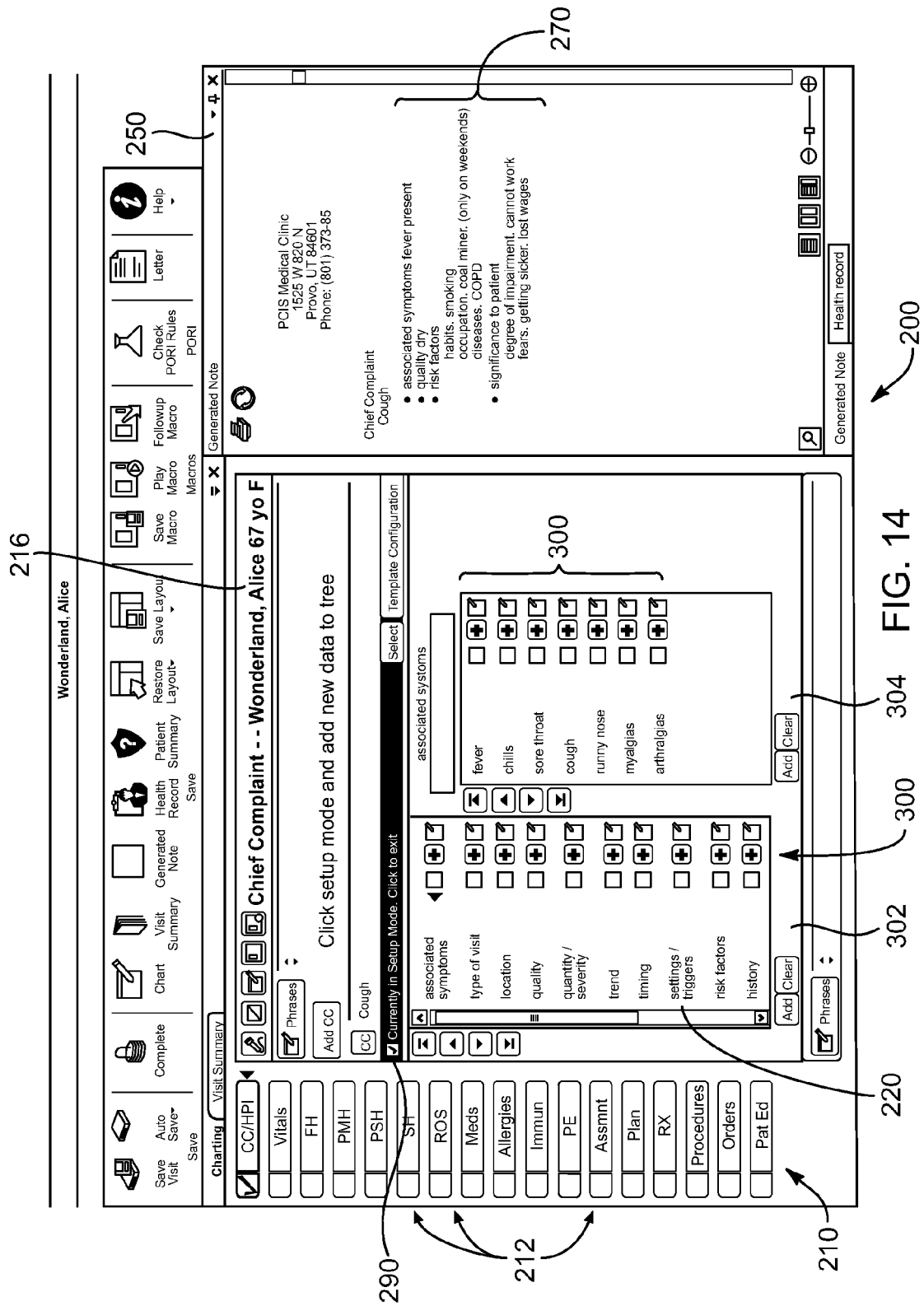

Referring now to FIG. 14, a healthcare provider may edit sub-form 216 by selecting setup mode 290. Upon entering setup mode, additional options 300 are provided whereby the user may select, add, delete, edit or modify the selections of sub-form 216. One of skill in the art will appreciate that the patient form 200 may also include editing feature to permit the user to modify the available sub-forms 212, as well as the general appearance and organization of the patient form 200. In some embodiments, the setup mode 290 enables the user to is available at any time such that the user may access the mode before, during or after the examination of the patient. Therefore, in the event that the healthcare provider determines that the patient form 200 requires a specific value to represent an observation or activity of the healthcare provider, the healthcare provider may quickly and easily modify the form 200 to enable such representation.

Once the setup mode 290 has been selected, the user may modify the patient form 200 using options 300. For example, if the healthcare provider determines that sub-form 216 needs a new patient category 220, the healthcare provider may scroll through the available categories 220 and add a new patient category using the editing options 300 associated with the patient category. Likewise, the user may modify an existing patient category by using the editing options 300 associated with the desired patient category. Upon selecting a new or existing patient category 220, the respective selectable options 232 for the selected category are displayed. When in the setup mode 290, these option 232 also display editing tools 300 whereby to make any necessary or desired changes.

Figure 17:
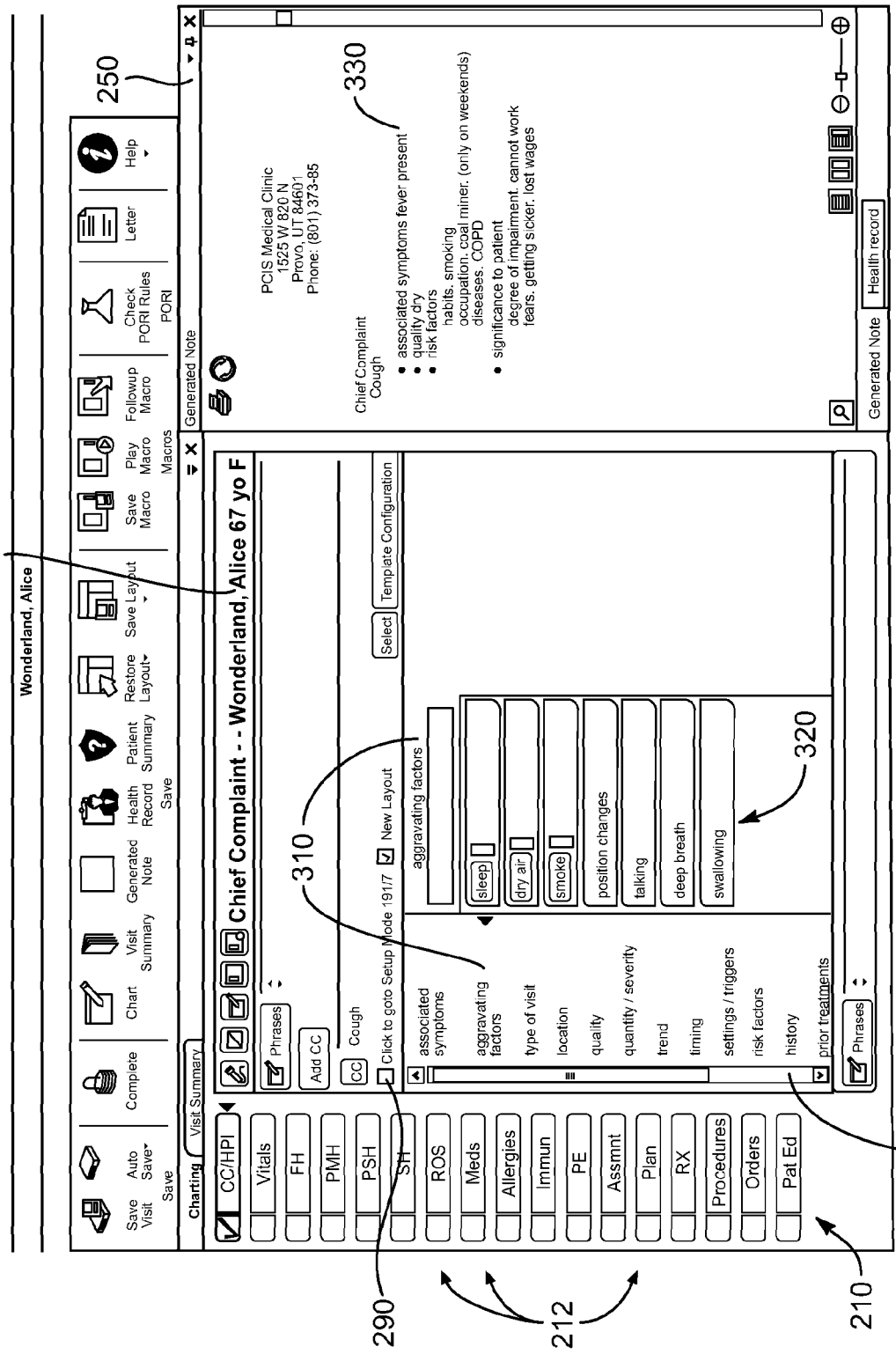

If the healthcare provider is unable to locate a desired patient category 220 or selectable option 232, the user may create a new category or option via the field 302 or 304, respectively. A new category or option is created by entering a desired name into the field 302 or 304 and then adding the name to the list, as shown in FIGS. 15 and 16. The user may further customize the new entry 310 by adding selectable option 320 using field 304. Upon the creation of a new category 310 and respective options 320, these new entries are recorded as discrete data points and linked to their respective levels within the patient form 200. Following the completion of the desired modifications, the setup mode 290 is exited by deselecting the setup mode 290 option. The user may then select the new category 310 and any relevant option 320 relating thereto. The selected category and options are then recorded as discrete data points and displayed as a new entry 330 in the patient summary sheet 250, as shown in FIG. 17.

FIGS. 18-21 illustrate various screenshots of an electronic patient form 340 and corresponding patient summary sheet 342 representing methods for customizing and updating the same instantaneously and in real-time in accordance with a representative embodiment of the present invention. Electronic patient form 340 has discrete data points at locations on a display that are reliable, predictive, and familiar to the particular healthcare provider or other user. Such familiarity allows the form 340 to be easily used. As information is input into the form 340, sheet 342 is automatically and instantaneously updated in real time. Thus, for example in FIG. 19, as information is recorded at input 344 relating to the patient's temperature, it is automatically and instantaneously updated in real-time at 346 of sheet 342. Similarly, in FIG. 20 as information is entered into the area 348 of form 340, it is automatically and instantaneously updated in real time at 350 of sheet 342. Similarly, in FIG. 21 as information is entered into the area 352 of form 340, it is automatically and instantaneously updated in real time at 354 of sheet 342.

While the present embodiment automatically and instantaneously updates the patient sheet in real-time when information is input into the customizable electronic patient form, other embodiments automatically and instantaneously update the customizable electronic patient form in real-time when input is provided into the patient sheet. In yet other embodiments, either the patient sheet or the patient form is automatically and instantaneously updated in real-time when the other receives input. The sheet provides a readable record for the patient.

Figure 22:
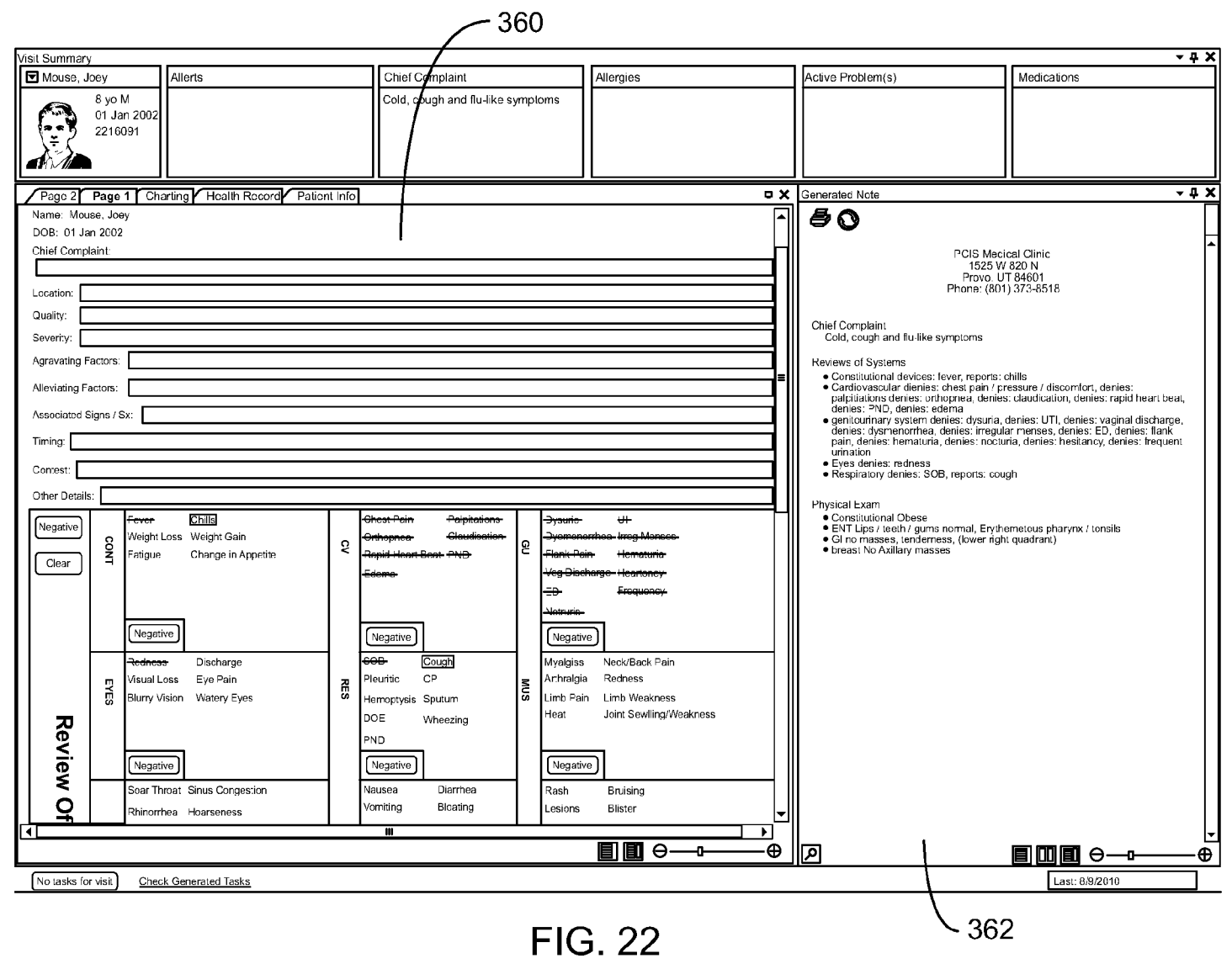
Figure 23:
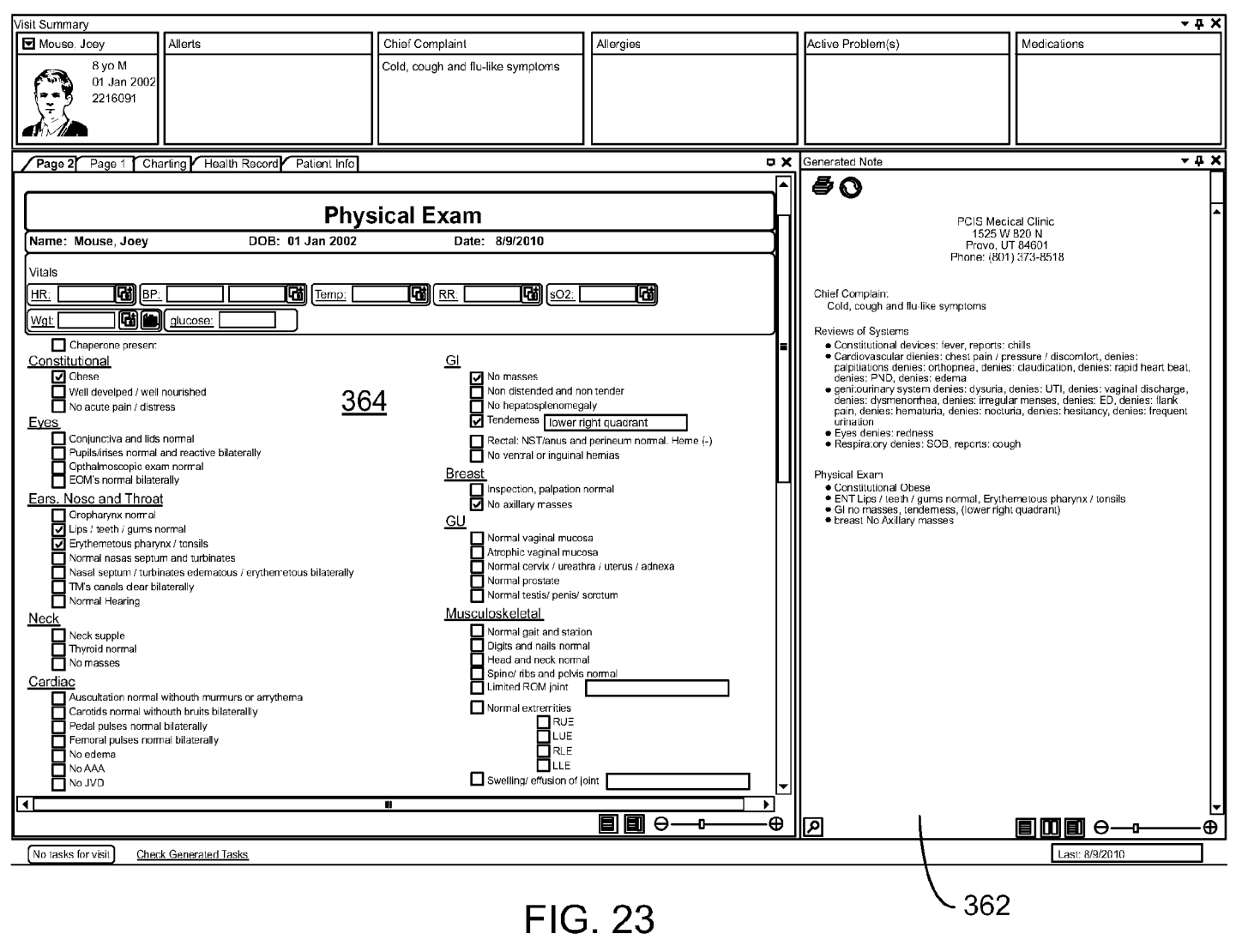

FIGS. 22-23 illustrate screenshots of another electronic patient form 360 and corresponding patient summary sheet 362 for customizing and updating the same instantaneously and in real-time, wherein the electronic patient form 360 has discrete data points at locations on a display that are reliable, predictive, and familiar to the healthcare provider or other user. As information is input into the form 360, sheet 362 is automatically and instantaneously updated in real-time. Form 364 is part of form 360, such as a second page of form 360.

Figure 24:
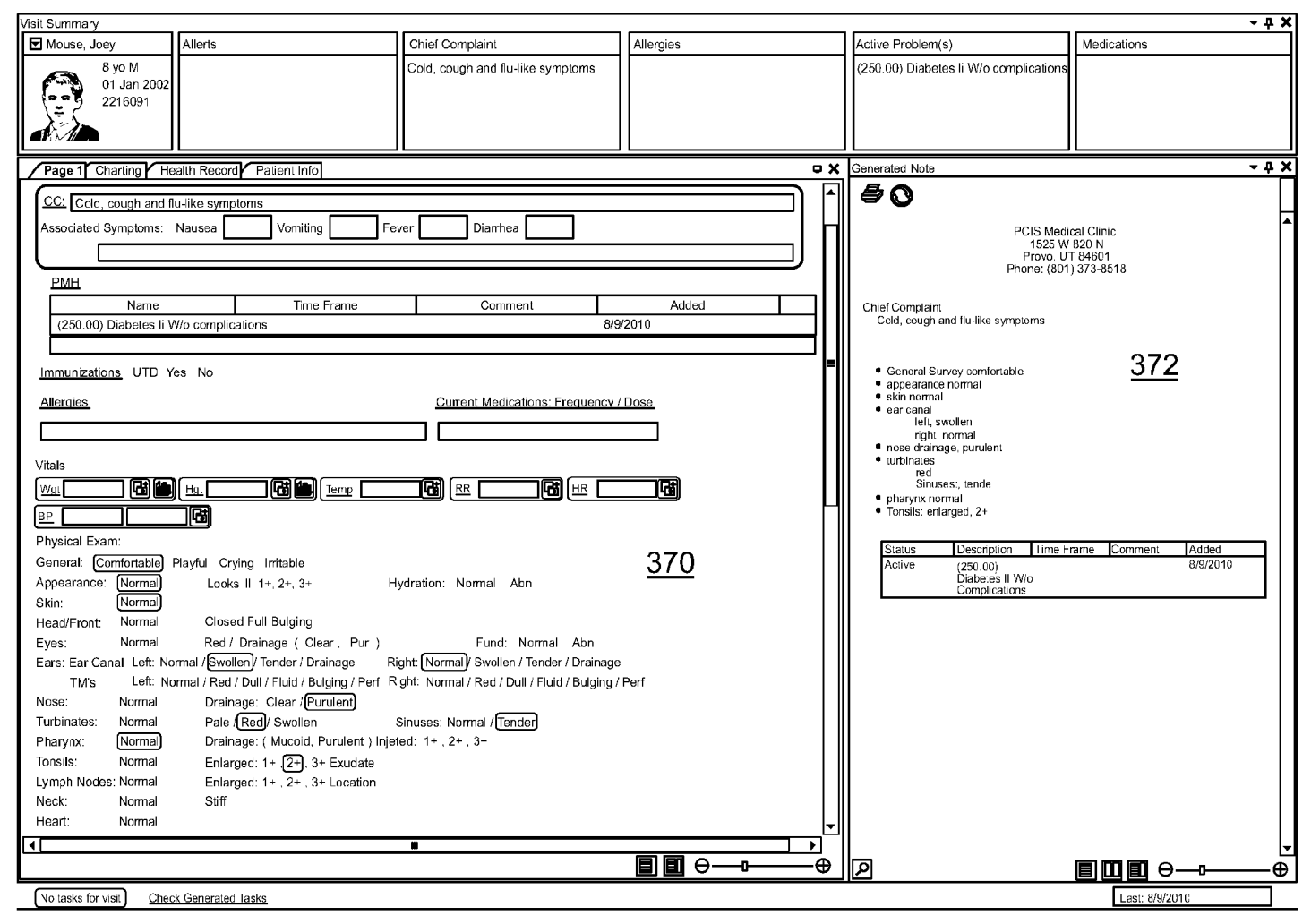

FIG. 24 illustrates a screenshot of another electronic patient form 370 and corresponding patient summary sheet 372 representing methods for customizing and updating the same instantaneously or in real-time in accordance with a representative embodiment of the present invention, wherein the electronic patient form has discrete data points at locations on a display that are reliable, predictive, and familiar to the healthcare provider or other user.

FIG. 25 illustrates a representative patient or visit form 380 utilized by a healthcare provider or other user such as during a patient conference and diagnosis in accordance with a representative embodiment of the present invention.

Figure 26:
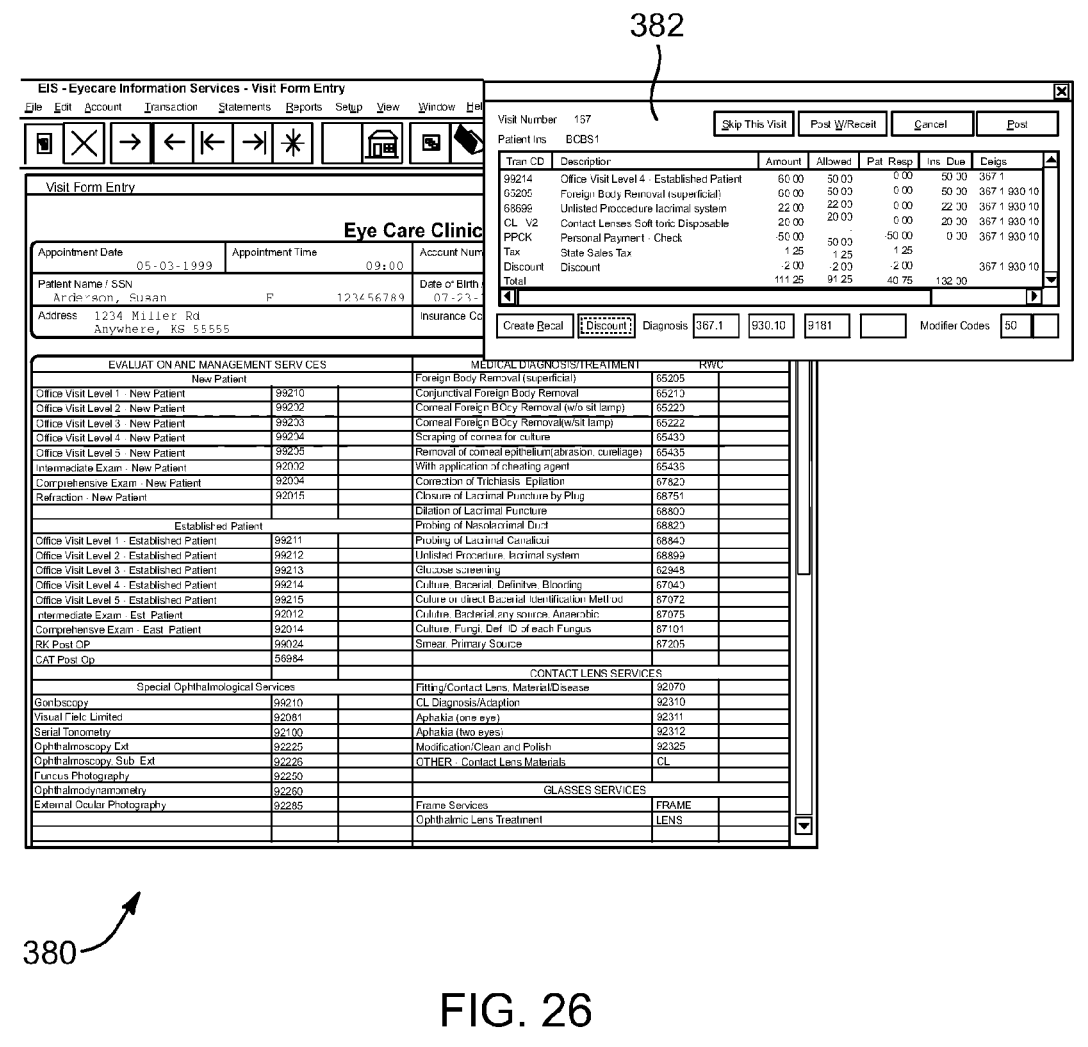

FIG. 26 illustrates the representative patient or visit form 380 having a visit summary feature 382 for use by a healthcare provider or other user during an office visit by a patient in accordance with a representative embodiment of the present invention.

FIG. 27 illustrates a representative record and billing summary printout 384 for the patient after a visit with the health care provider or agent.

FIG. 28 illustrates another representative patient or visit form 390 utilized by a healthcare provider or other user such as during a patient conference and diagnosis in accordance with a representative embodiment of the present invention.

FIG. 26 illustrates the representative patient or visit form 390 having a visit form posting or visit summary feature 400 for use by a healthcare provider or other user during an office visit by a patient in accordance with a representative embodiment of the present invention.

In at least some embodiments of the present invention, a patient identifies a healthcare provider and/or provides the chief complaint or reason for the visit to the clinic or location of the healthcare provider. A dynamic and customizable electronic input form is generated and displayed for the healthcare provider based on the provider and the chief complaint of the patient. A previous visit form can be displayed for assistance in decision making. A healthcare provider or medical assistant records on the dynamic and customizable form findings (such as patient blood pressure, temperature, etc.), information relating to the chief complaint, procedures performed, orders needed (such as to a laboratory or radiology), future plans (such as surgeries needed, next appointment, future recall, etc.), and/or medications/prescriptions (including the generation of an electronic prescription that is sent out for filling at a pharmacy). All information is recording not only in the visit form but also is simultaneously recorded in real-time on a patient history or log. In one embodiment, the patient history or log is visible to the user at the same time that the visit form is visible to the user. In another embodiment, the patient history or log is not visible, but is being generated instantaneously in real-time in the background while the patient visit form is being filled out. Information is gathered and displayed in real-time.

Thus, embodiments of the present invention relate generally to maintaining medical and billing records of patients within a health care organization and, more specifically, to maintaining and updating medical records in a computer networked system, including patient medical records and billing records. The present invention further relates to systems and methods that provide simultaneous tracking of activities relating to patient care by recording healthcare events as discrete data points that are simultaneously displayed in the patient record and shown as entries in a generated note or patient summary sheet. Embodiments of the present invention embrace systems and methods relating to electronic medical records as well as practice management records, including medical billing records.

The present invention may be embodied in other specific forms without departing from its spirit or essential characteristics. The described embodiments are to be considered in all respects only as illustrated and not restrictive. For example, although the specific embodiments have been limited to application in the medical services industry, the invention has broader applications to industries that do not include medical services. This can include insurance companies that have insured clients meet during an office visit to review policies, values, claims and the like. The scope of the invention is, therefore, indicated by the appended claims rather than by the foregoing description. All changes which come within the meaning and range of equivalency of the claims are to be embraced within their scope.

What is claimed is:

1. In a computer processing system that is configured to be associated with healthcare services, a method for generating, displaying and recording healthcare service information, the method comprising:
rendering a user interface that includes a patient form and a data logger on an output device of the computer processing system, wherein the patient form includes a plurality of selectable user interface elements, each selectable user interface element representing a patient healthcare parameter, and wherein the data logger comprises an electronically generated note that displays summary details regarding changes made to the patient form;
receiving user input to the patient form that selects a first of the plurality of selectable user interface elements;
receiving user input to a second of the plurality of selectable user interface elements that provides a value for the patient healthcare parameter associated with the first user interface element;
automatically creating a first and a second entry in the data logger, the first entry identifying the patient healthcare parameter associated with the first user interface element, the second entry identifying the value provided for the patient healthcare parameter associated with the first user interface element;
linking the first entry in the data logger with the first user interface element and the second entry in the data logger with the second user interface element;
receiving user input that selects the second entry in the data logger;
in response to the user input that selects the second entry in the data logger, displaying the second user interface element in the patient form of the user interface and moving focus of the user interface to the second user interface element to enable the user to directly modify the second user interface element without requiring navigation to the second user interface element;
receiving input that modifies the value in the second user interface element; and
in response to receiving input that modifies the value in the second user interface element, automatically updating the second entry in accordance with the modification to the value.

2. The method of claim 1, wherein the patient healthcare parameter is selected from at least one of a physical, a mental, a psychological, an emotional, a mechanical, a structural, a pharmaceutical, a chemical and a medical characteristic of a patient.

3. The method of claim 2, wherein the value comprises a number selected from a scale.

4. The method of claim 2, wherein the value comprises at least one of an indication, a condition, a size, a quantity, a color, a temperature, a shape, an observation, a sound, a photograph, a scan, a radiograph image, a chart, a graph, a texture, a scent, a viscosity, a consistency, a time, a length, a reference indicator, a gender, a sexual orientation, an age, an allergy, a reaction, a number, and a letter.

5. A medical information system comprising:
one or more processors; and
memory storing computer executable instructions which when executed perform a method for facilitating the input of patient information to a user interface, the method comprising:
rendering a user interface that includes a patient form and a data logger on an output device of the computer processing system, wherein the patient form includes a plurality of selectable user interface elements, each selectable user interface element representing a patient healthcare parameter, and wherein the data logger comprises an electronically generated note that displays summary details regarding changes made to the patient form;
receiving user input to the patient form that selects a first of the plurality of selectable user interface elements;
receiving user input to a second of the plurality of selectable user interface elements that provides a value for the patient healthcare parameter associated with the first user interface element;
automatically creating a first and a second entry in the data logger, the first entry identifying the patient healthcare parameter associated with the first user interface element, the second entry identifying the value provided for the patient healthcare parameter associated with the first user interface element;

linking the first entry in the data logger with the first user interface element and the second entry in the data logger with the second user interface element;

receiving user input that selects the second entry in the data logger;

in response to the user input that selects the second entry in the data logger, displaying the second user interface element in the patient form of the user interface and moving focus of the user interface to the second user interface element to enable the user to directly modify the second user interface element without requiring navigation to the second user interface element;

receiving input that modifies the value in the second user interface element; and in response to receiving input that modifies the value in the second user interface element, automatically updating the second entry in accordance with the modification to the value.

6. The medical information system of claim 5, wherein the plurality of selectable user interface elements that are displayed in the patient form is customizable by adding or removing user interface elements.

7. The medical information system of claim 5, wherein the patient healthcare parameter associated with the first user interface element comprises a parameter of a patient's chief complaint.

8. A computer program product comprising one or more non-transitory computer readable media having storing thereon computer executable instructions which when executed perform a method for generating, displaying and recording healthcare service information, the method comprising:

rendering a user interface that includes a patient form and a data logger on an output device of the computer processing system, wherein the patient form includes a plurality of selectable user interface elements, each selectable user interface element representing a patient healthcare parameter, and wherein the data logger comprises an electronically generated note that displays summary details regarding changes made to the patient form;

receiving user input to the patient form that selects a first of the plurality of selectable user interface elements;

receiving user input to a second of the plurality of selectable user interface elements that provides a value for the patient healthcare parameter associated with the first user interface element;

automatically creating a first and a second entry in the data logger, the first entry identifying the patient healthcare parameter associated with the first user interface element, the second entry identifying the value provided for the patient healthcare parameter associated with the first user interface element;

linking the first entry in the data logger with the first user interface element and the second entry in the data logger with the second user interface element;

receiving user input that selects the second entry in the data logger;

in response to the user input that selects the second entry in the data logger, displaying the second user interface element in the patient form of the user interface and moving focus of the user interface to the second user interface element to enable the user to directly modify the second user interface element without requiring navigation to the second user interface element;

receiving input that modifies the value in the second user interface element; and in response to receiving input that modifies the value in the second user interface element, automatically updating the second entry in accordance with the modification to the value.

9. The computer program product of claim 8, wherein the data logger comprises an electronic patient summary sheet.

10. The computer program product of claim 8, wherein the value comprises a number selected from a scale.

11. The computer program product of claim 10, wherein the scale corresponds to a diagnostic range for the patient healthcare parameter.

12. The computer program product of claim 8, wherein the value comprises at least one of an indication, a condition, a size, a quantity, a color, a temperature, a shape, an observation, a sound, a photograph, a scan, a radiograph image, a chart, a graph, a texture, a scent, a viscosity, a consistency, a time, a length, a reference indicator, a gender, a sexual orientation, an age, an allergy, a reaction, a number, and a letter.

13. The computer program product of claim 8, wherein the patient healthcare parameter is selected from at least one of a physical, a mental, a psychological, an emotional, a mechanical, a structural, a pharmaceutical, a chemical and a medical characteristic of a patient.

* * * * *